(12) United States Patent
Furusaki

(10) Patent No.: US 10,450,210 B2
(45) Date of Patent: *Oct. 22, 2019

(54) MINERAL FUNCTIONAL WATER, METHOD FOR PRODUCING THE SAME

(71) Applicants: Riken Techno System Co., Ltd., Fukuoka (JP); Santa Mineral Co., Ltd., Tokyo (JP)

(72) Inventor: Koichi Furusaki, Fukuoka (JP)

(73) Assignees: Riken Techno System Co., Ltd., Fukuoka (JP); Santa Mineral Co., Ltd., Tokyo (JP)

( * ) Notice: Subject to any disclaimer, the term of this patent is extended or adjusted under 35 U.S.C. 154(b) by 32 days.

This patent is subject to a terminal disclaimer.

(21) Appl. No.: 15/706,053

(22) Filed: Sep. 15, 2017

(65) Prior Publication Data

US 2018/0016168 A1 Jan. 18, 2018

Related U.S. Application Data

(63) Continuation of application No. PCT/JP2016/058362, filed on Mar. 16, 2016.

(30) Foreign Application Priority Data

Mar. 17, 2015 (JP) ................................ 2015-053971

(51) Int. Cl.
| | |
|---|---|
| C02F 1/68 | (2006.01) |
| A61K 35/02 | (2015.01) |
| A61K 35/614 | (2015.01) |
| A61K 35/618 | (2015.01) |
| A61K 36/185 | (2006.01) |
| A61K 36/20 | (2006.01) |
| A61K 36/28 | (2006.01) |
| A61K 36/282 | (2006.01) |
| A61K 36/73 | (2006.01) |
| A61K 36/738 | (2006.01) |
| C02F 1/30 | (2006.01) |
| C02F 1/36 | (2006.01) |
| C02F 1/48 | (2006.01) |
| A61K 36/14 | (2006.01) |

(52) U.S. Cl.
CPC ............... *C02F 1/68* (2013.01); *A61K 35/02* (2013.01); *A61K 35/614* (2013.01); *A61K 35/618* (2013.01); *A61K 36/14* (2013.01); *A61K 36/185* (2013.01); *A61K 36/20* (2013.01); *A61K 36/28* (2013.01); *A61K 36/282* (2013.01); *A61K 36/73* (2013.01); *A61K 36/738* (2013.01); *C02F 1/30* (2013.01); *C02F 1/36* (2013.01); *C02F 1/48* (2013.01)

(58) Field of Classification Search
None
See application file for complete search history.

(56) References Cited

U.S. PATENT DOCUMENTS

| | | | |
|---|---|---|---|
| 7,344,740 B2 * | 3/2008 | Vail, III | A61K 36/534 424/747 |
| 2017/0118995 A1* | 5/2017 | Furusaki | A61K 36/28 |
| 2018/0044602 A1* | 2/2018 | Furusaki | C02F 1/36 |

FOREIGN PATENT DOCUMENTS

| | | |
|---|---|---|
| JP | 2007-144313 A | 6/2007 |
| JP | 2008-308573 A | 12/2008 |
| JP | 2011-056366 A | 3/2011 |
| JP | 4817817 B | 11/2011 |
| JP | 5864010 B | 2/2016 |
| WO | 2016/043213 A1 | 3/2016 |
| WO | 2016/043214 A1 | 3/2016 |

OTHER PUBLICATIONS

International Search Report issued in PCT/JP2016/058362, dated Jun. 7, 2016, with English translation (7 pages).
Written Opinion of International Search Authority issued in PCT/JP2016/058362, dated Jun. 7, 2016 (5 pages).

* cited by examiner

Primary Examiner — Ralph J Gitomer
(74) Attorney, Agent, or Firm — Nakanishi IP Associates, LLC

(57) ABSTRACT

Provided is a method of producing mineral function water showing beneficial effects, such as antioxidant effects, or the like. The water including contains mineral-containing water (A) and mineral-containing water (B) according to a ratio of 1:5 to 1:20 (weight ratio), the mineral-containing water (A) containing first mineral components eluted from mineral-imparting material (A) containing: vegetation raw material, woody plant raw material, and sulfur raw material, the mineral-containing water (B) containing second mineral-containing water (B) containing the mineral component eluted from inorganic mineral-imparting material (B).

3 Claims, 12 Drawing Sheets

MINERAL FUNCTIONAL WATER, METHOD FOR PRODUCING THE SAME

CROSS-REFERENCE TO RELATED APPLICATIONS

The present application is a continuation application of International Patent Application No. PCT/JP2016/058362 filed on Mar. 16, 2016, which claims priority to Japanese Patent Application No. 2015-053971 filed on Mar. 17, 2015, the entire contents of which are incorporated by reference.

BACKGROUND OF THE INVENTION

1. Field of the Invention

The present invention relates to mineral functional water including beneficial effects, such as antioxidant effects, and application products of the same.

2. Description of the Related Art

It is supposed that mineral-containing water may show effects including: soil-modifying action; plant-growing action; haiinful organic substance-decomposing action; deodorizing action; and air-cleaning action. Conventionally, various kinds of mineral-containing water and/or equipment for producing mineral-containing water have been developed.

The present inventors have developed a mineral-containing water-producing apparatus (A) including:
 a unit for immersing a conductive wire covered with insulator and mineral-imparting material (A) in water, conducting DC electric current to the conductive wire to generate water flow around the conductive wire in the same direction as the DC electric current, applying ultrasonic vibration to the water, thereby forming raw mineral water solution (A); and
 a far-infrared ray-generating unit irradiating far-infrared rays to the formed raw mineral water solution (A) to produce mineral-containing water (A) (See, Reference 1.).

The present inventors also have developed mineral functional water-producing equipment including:
 a mineral-containing water-producing apparatus (A);
 a plurality of water-passing containers into which different kinds of mineral-imparting material (B) from each other is filled up;
 a water supply passage communicating with the plurality of water-passing containers in series;
 a roundabout channel connected to the water supply passage in a state where the roundabout channel is parallel to the plurality of water-passing containers, respectively; and
 a water stream-changing valve provided in branch parts between the water supply passage and the roundabout channel, respectively (See, Reference 2.).

The present inventors have also reported that upon using the mineral functional water-producing equipment, mineral functional water (far-infrared ray-generating water) with functions of generating far-infrared rays of specific wavelength can be produced.

The present inventors have repeatedly studied kinds and mixing ratios of mineral-imparting material while using the mineral functional water-producing apparatus disclosed in Reference 2, and have reported that mineral functional water produced under a specific condition shows excellent controlling effects upon unicellular organisms and/or viruses (See, Reference 3.).

REFERENCES

Reference 1: Japan registered patent No. 4817817.
Reference 2: Japanese patent application Laid-open No. 2011-56366
Reference 3: Japanese registered patent No. 5864010.

OBJECTS AND SUMMARY OF THE INVENTION

As mentioned above, various kinds of mineral-containing water have been reported in the past. Many of effects showed by mineral-containing water have not been scientifically proven, and true action of the mineral-containing water also has been not yet made clear in some respects.

In many cases, conventional mineral-containing water may not actually show advertised effects, may merely show effects which are insufficient for practical use, or, may has poor reproducibility of the effects.

With respect to even the mineral functional water produced using the device reported in References 1 and 2, it cannot be said that the target of the mineral functional water manifesting enough effects can surely be produced.

In particular, kinds and mixing ratios of material components (mineral-imparting material) used in the mineral-containing water-producing apparatuses (A) and (B) intricately concern. In fact, relationships between a kind of used mineral-imparting material and effects showed by obtained mineral functional water are not always proven.

In view of the above conditions, an object of the present invention is to provide mineral functional water capable of showing beneficial effects that have not been discovered yet.

Using the mineral functional water-producing equipment disclosed in Reference 2, the present inventors have repeated consideration mainly focusing on the kinds and the mixing ratios of mineral-imparting material.

Finally, the present inventors have found out that the mineral functional water produced under a certain specific condition using raw material containing sulfur raw material manifests antioxidant effects, thereby having devised the present invention.

That is, the present invention concerns the following inventions.

Item [1]: A method of producing mineral functional water, comprising:
 producing first mineral-containing water (A) according to the following first process (1): and
 producing second mineral-containing water (B) according to the following second process (2):
 the mineral functional water containing the first produced mineral-containing water (A) and the second produced mineral-containing water (B) according to a ratio within a range of 1:5-1:20 (weight ratio),
 wherein the first process (1) includes:
 immersing a conductive wire covered with insulator and mineral-imparting material (A) into water, the mineral-imparting material containing: woody plant raw material; vegetation raw material; and sulfur raw material, the vegetation raw material including: vegetation belonging to Asteraceae and vegetation belonging to Rosaceae, the woody plant raw material including at least one kind selected from a group consisting of *Maple, Betula platyphylla, Pinus*, and *Cryptomeria japonica*;

conducting DC electric current to the conductive wire to generate water flow around the conductive wire in the same direction as the DC electric current, applying ultrasonic vibration to the water, thereby forming raw mineral water solution (A); and irradiating far-infrared rays (wavelength of 6-14 micrometers) to the raw mineral water solution (A) to form mineral-containing water (A), and wherein the second process (2) uses six connected in series water-passing containers in which different kinds of inorganic mineral-imparting material (B) from each other is filled, the six water-passing containers including: a first water-passing container; a second water-passing container; a third water-passing container; a fourth water-passing container; a fifth water-passing container; and a sixth water-passing container, wherein:

the mineral-imparting material (B1) filled into the first water-passing container is mixture including: 70 weight % of lime stone; 15 weight % of fossil coral; and 15 weight % of shell, respectively;

the mineral-imparting material (B2) filled into the second water-passing container is mixture including: 40 weight % of lime stone; 15 weight % of fossil coral; 40 weight % of shell; and 5 weight % of activated carbon, respectively;

the mineral-imparting material (B3) filled into the third water-passing container is mixture including: 80 weight % of lime stone; 15 weight % of fossil coral; and 5 weight % of shell, respectively;

the mineral-imparting material (B4) filled into the fourth water-passing container is mixture including: 90 weight % of lime stone; 5 weight % of fossil coral; and 5 weight % of shell, respectively;

the mineral-imparting material (B5) filled into the fifth water-passing container is mixture including: 80 weight % of lime stone; 10 weight % of fossil coral; and 10 weight % of shell, respectively; and the mineral-imparting material (B6) filled into the sixth water-passing container is mixture including: 60 weight % of lime stone; 30 weight % of fossil coral; and 10 weight % of shell, respectively, and making the water pass through the six water-passing containers to form mineral-containing water (B).

Item [2]: The method of producing mineral functional water as defined in Item 1, wherein:

10 to 15 weight % of the mineral-imparting material (A) based on the water is added; and the DC electric current conducted to the conductive wire has 0.05-0.1 A of a current value and 8000-8600 V of a voltage value, respectively.

Item [3]: The method of producing mineral functional water as defined in any of Items 1 to 2, wherein:

dried pulverized product of Asteraceae plants and dried pulverized product of Rosaceae plants are used as the mineral-imparting material (A);

the dried pulverized product of the Asteraceae plants is produced by:

mixing 10 weight % of *Cirsium japonicum* (leaf parts, stein parts and flower parts thereof), 60 weight % of *Artemisia indica* (leaf parts and stem parts thereof) and 30 weight % of *Farfugium japonicum* (leaf parts and stem parts thereof), respectively to produce first mixture thereof; making the first mixture dry; and then pulverizing the dried first mixture;

the dried pulverized product of the Rosaceae plants is produced by:

mixing 20 weight % of *Rosa multiflora* (leaf parts and flower parts thereof), 10 weight % of *Geum japonicum* (leaf parts and stem parts thereof), and 70 weight % of *Rubus* L. (leaf parts, stem parts, and flower parts thereof), respectively to produce second mixture thereof; making the second mixture dry; and then pulverizing the dried second mixture;

the dried pulverized product of the Asteraceae plants and the dried pulverized product of the Rosaceae plants are mixed according to 1:1 (weight ratio) to obtain vegetation raw material (A1);

the woody plant raw material (A2) is produced by:

mixing 20 weight % of *Maple* (fallen leaf parts and stem parts thereof), 60 weight % of *Betula platyphylla* (fallen leaf parts, stem parts, and bark parts thereof), and 20 weight % of *Cryptomeria japonica* (fallen leaf parts, stem parts, and bark parts thereof) to produce third mixture; making the third mixture dry; and then pulverizing the dried third mixture; and the sulfur raw material is composed of volcanic sulfur (A3); and mineral-imparting material (A') is obtained by:

mixing the vegetation raw material (A1) and the woody plant raw material (A2) according to 1:5 (weight ratio) to produce plant mixture; and based on 100 pts.wt. of the plant mixture, mixing 2-8 weight % of the volcanic sulfur (A3).

Preferable Embodiments of the mineral functional water according to the present invention concern the first invention [X1] and the second invention [X2], each of which is a producing method as specified below.

The mineral functional water according to the second invention[X2] corresponds to mineral functional water in Example 1 mentioned later.

[X1]: Mineral functional water produced by a method comprising:

producing first mineral-containing water (A) according to the following first process (1): and producing second mineral-containing water (B) according to the following second process (2):

the mineral functional water containing the first produced mineral-containing water (A) and the second produced mineral-containing water (B) according to a ratio within a range of 1:5-1:20 (weight ratio), wherein the first process (1) includes:

immersing a conductive wire covered with insulator and mineral-imparting material (A) into water, the mineral-imparting material containing: woody plant raw material; and vegetation raw material; the vegetation raw material including: vegetation belonging to Asteraceae and vegetation belonging to Rosaceae, the woody plant raw material including at least one kind selected from a group consisting of *Maple, Betula platyphylla, Pinus*, and *Cryptomeria japonica*;

conducting DC electric current to the conductive wire to generate water flow around the conductive wire in the same direction as the DC electric current, applying ultrasonic vibration to the water, thereby forming raw mineral water solution (A); and irradiating far-infrared rays (wavelength of 6-14 micrometers) to the raw mineral water solution (A) to form mineral-containing water (A), and wherein 10 to 15 weight % of the mineral-imparting material (A) based on the water is added; and the DC electric current conducted to the conductive wire has 0.05-0.1 A of a current value and 8000-8600 V of a voltage value, respectively, wherein:

dried pulverized product of Asteraceae plants and dried pulverized product of Rosaceae plants are used as the mineral-imparting material (A);

the dried pulverized product of the Asteraceae plants is produced by:

mixing 10 weight % of *Cirsium japonicum* (leaf parts, stem parts and flower parts thereof), 60 weight % of *Artemisia indica* (leaf parts and stem parts thereof) and 30 weight % of *Farfugium japonicum* (leaf parts and stem parts thereof), respectively to produce first mixture thereof; making the first mixture dry; and then pulverizing the dried first mixture;

the dried pulverized product of the Rosaceae plants is produced by:

mixing 20 weight % of *Rosa multiflora* (leaf parts and flower parts thereof), 10 weight % of *Geum japonicum* (leaf parts and stem parts thereof), and 70 weight % of *Rubus* L. (leaf parts, stem parts, and flower parts thereof), respectively to produce second mixture thereof; making the second mixture dry; and then pulverizing the dried second mixture:

the dried pulverized product of the Asteraceae plants and the dried pulverized product of the Rosaceae plants are mixed according to 1:1 (weight ratio) to obtain vegetation raw material (A1);

the woody plant raw material (A2) is produced by:

mixing 20 weight % of *Maple* (fallen leaf parts and stem parts thereof), 60 weight % of *Betula platyphylla* (fallen leaf parts, stem parts, and bark parts thereof), and 20 weight % of *Cryptomeria japonica* (fallen leaf parts, stem parts, and bark parts thereof) to produce third mixture; making the third mixture dry; and then pulverizing the dried third mixture; and sulfur raw material is composed of volcanic sulfur (A3); and mineral-imparting material (A') is obtained by:

mixing the vegetation raw material (A1) and the woody plant raw material (A2) according to 1:5 (weight ratio) to produce plant mixture; and based on 100 pts.wt. of the plant mixture, mixing 2-8 weight % of the volcanic sulfur (A3)

wherein the second process (2) uses six connected in series water-passing containers in which different kinds of inorganic mineral-imparting material (B) from each other is filled, the six water-passing containers including: a first water-passing container; a second water-passing container; a third water-passing container; a fourth water-passing container; a fifth water-passing container; and a sixth water-passing container, wherein:

the mineral-imparting material (B1) filled into the first water-passing container is mixture including: 70 weight % of lime stone; 15 weight % of fossil coral; and 15 weight % of shell, respectively;

the mineral-imparting material (B2) filled into the second water-passing container is mixture including: 40 weight % of lime stone; 15 weight % of fossil coral; 40 weight % of shell; and 5 weight % of activated carbon, respectively;

the mineral-imparting material (B3) filled into the third water-passing container is mixture including: 80 weight % of lime stone; 15 weight % of fossil coral; and 5 weight % of shell, respectively;

the mineral-imparting material (B4) filled into the fourth water-passing container is mixture including: 90 weight % of lime stone; 5 weight % of fossil coral; and 5 weight % of shell, respectively;

the mineral-imparting material (B5) filled into the fifth water-passing container is mixture including: 80 weight % of lime stone; 10 weight % of fossil coral; and 10 weight % of shell, respectively; and the mineral-imparting material (B6) filled into the sixth water-passing container is mixture including: 60 weight % of lime stone; 30 weight % of fossil coral; and 10 weight % of shell, respectively, and making the water pass through the six water-passing containers to form mineral-containing water (B).

[X2]: The mineral functional water as defined in Item X1, wherein the first produced mineral-containing water (A) and the second produced mineral-containing water (B) are mixed according to a ratio within a range of 1:10 (weight ratio).

[X3] The mineral functional water as defined in any one of Items X1 to X2, further including antioxidant effects.

[X4] The mineral functional water as defined in any one of Items X1 to X3, further including scavenging activity on superoxide.

[X5] Composition containing the mineral functional water as defined in any one of Items X1 to X4.

[X6] The composition as defined in Item X5, wherein the composition is used as medicinal composition.

[X7] The composition as defined in Item X6, wherein the composition is used as prophylactic therapeutic agent for diseases caused by active oxygen and/or free radicals.

[X8] The composition as defined in any one of Items X6 to X7, wherein the composition is used as a prophylactic therapeutic agent for skin diseases.

[X8] The composition as defined in Item X5, wherein the composition is used as additives for food and/or drink.

[X9] The composition as defined in Item X5, wherein the composition is used as cosmetic material composition.

Effect of Invention

The present invention provides mineral functional water including beneficial performance, such as antioxidant effects.

BRIEF EXPLANATION OF SYMBOLS

Figure 1:
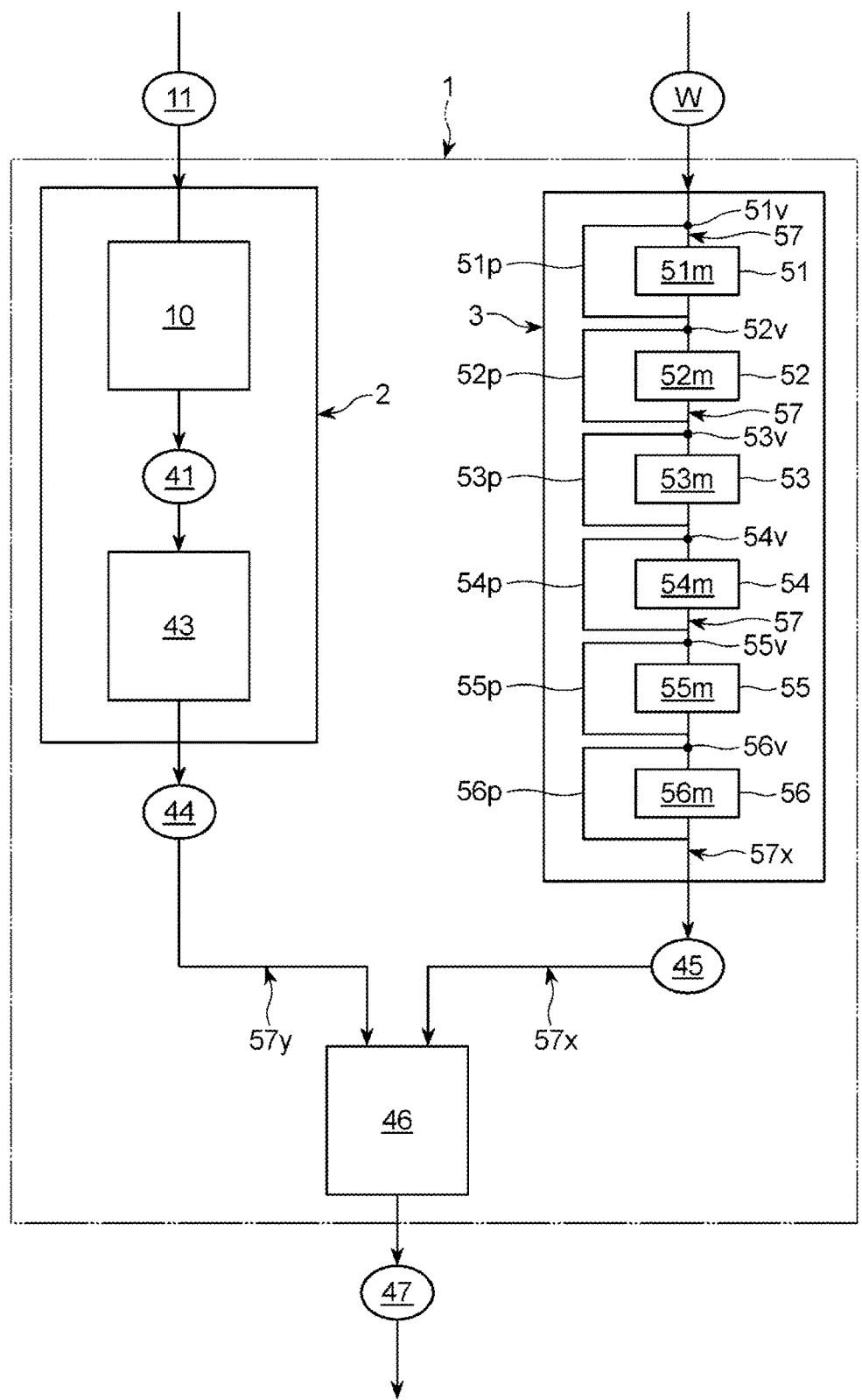
FIG. 1 is a block diagram showing a schematic structure of mineral functional water-producing equipment.

1: mineral functional water-producing equipment
2: mineral-containing water (A) producing apparatus
3: mineral-containing water (B) producing apparatus
10: raw mineral water solution production unit
11, W: water
12: mineral-imparting material (A)
13: reaction vessel
13$a$: wall body
14: insulator
15: conductive wire
16: ultrasonic wave generation unit
17: DC power supply device
18$a$, 18$b$, 18$c$: circulating passage
19: drain port
20, 23: opening control valve
21, 25: drain valve
22: housing tank
24: drain pipe
26: water temperature gage
29, 29$a$-29$g$, 29$s$, 29$t$: conductive cable
30: terminal
31: housing container
31$f$: hook
40: treatment container
41: raw mineral water solution (A)
42: agitation blade
43: far-infrared ray-generating unit
44: mineral-containing water (A)
45: mineral-containing water (B)
46: mixing tank
47: mineral functional water
51: first water-passing container
52: second water-passing container
53: third water-passing container
54: fourth water-passing container
55: fifth water-passing container
56: sixth water-passing container
51$a$-56$a$: main body part
51$b$-56$b$: switching button
51$c$-56$c$: axial center
51$d$-56$d$: lid body
51$f$-56$f$ flange part
51$m$-56$m$: mineral-imparting material (B)
51$p$-56$p$: roundabout channel
51$v$-56$v$: water stream-changing valve
57, 57$x$, 57$y$: water-supply passage
57$a$: water inlet
57$b$: water outlet
57$c$: mesh strainer
57$d$: automatic air valve
58: operation panel
59: signal cable
60: support frame
61: caster
62: level adjuster
63: raw water tank
DC: direct electric current
DW: tap water
R: water flow

DETAILED DESCRIPTION OF THE PREFERRED EMBODIMENTS

Hereinafter, with reference to the accompanying drawings, the present invention will now be explained while adducing some examples. The present invention, however, is not limited to the examples, and may be arbitrarily modified and/or changed within the scope of the present invention.

In addition, in this specification, the symbol of "-" is used for expression that means containing values and/or physical quantity below and over thereof.

In this specification, the words of "A and/or B" mean at least one of: either A or B; and both A and B. That is, the words of "A and/or B" includes: only A; only B; and both A and B.

[1. Mineral Functional Water According to the Present Invention]

Mineral functional water produced by a method comprising:
   producing first mineral-containing water (A) according to the following first process (1):
   producing second mineral-containing water (B) according to the following second process (2): and
   the mineral functional water containing the first produced mineral-containing water (A) and the second produced mineral-containing water (B) according to a ratio within a range of 1:5-1:20 (weight ratio).

Wherein the first process (1) includes:
   immersing a conductive wire covered with insulator and mineral-imparting material (A) into water, the mineral-imparting material containing: woody plant raw material; and vegetation raw material; the vegetation raw material including: vegetation belonging to Asteraceae and vegetation belonging to Rosaceae, the woody plant raw material including at least one kind selected from a group consisting of *Maple, Betula platyphylla, Pinus*, and *Cryptomeria japonica;*
   conducting DC electric current to the conductive wire to generate water flow around the conductive wire in the same direction as the DC electric current, applying ultrasonic vibration to the water, thereby forming raw mineral water solution (A); and
   irradiating far-infrared rays (wavelength of 6-14 micrometers) to the raw mineral water solution (A) to form mineral-containing water (A).

Wherein the second process (2) uses six connected in series water-passing containers in which different kinds of inorganic mineral-imparting material (B) from each other is filled, the six water-passing containers including: a first water-passing container; a second water-passing container; a third water-passing container; a fourth water-passing container; a fifth water-passing container; and a sixth water-passing container, wherein:

the mineral-imparting material (B1) filled into the first water-passing container is mixture including: 70 weight % of lime stone; 15 weight % of fossil coral; and 15 weight % of shell, respectively;

the mineral-imparting material (B2) filled into the second water-passing container is mixture including: 40 weight % of lime stone; 15 weight % of fossil coral; 40 weight % of shell; and 5 weight % of activated carbon, respectively;

the mineral-imparting material (B3) filled into the third water-passing container is mixture including: 80 weight % of lime stone; 15 weight % of fossil coral; and 5 weight % of shell, respectively;

the mineral-imparting material (B4) filled into the fourth water-passing container is mixture including: 90 weight % of lime stone; 5 weight % of fossil coral; and 5 weight % of shell, respectively;

the mineral-imparting material (B5) filled into the fifth water-passing container is mixture including: 80 weight % of lime stone; 10 weight % of fossil coral; and 10 weight % of shell, respectively; and the mineral-imparting material (B6) filled into the sixth water-passing container is mixture including: 60 weight % of lime stone; 30 weight % of fossil coral; and 10 weight % of shell, respectively, and making the water pass through the six water-passing containers to form mineral-containing water (B).

The raw material of the mineral functional water according to the present invention and a method for producing the same will be later explained in paragraphs related to [3. Method of producing mineral functional water according to the present invention].

The mineral functional water according to the present invention contains at least sulfur as a mineral component to show antioxidant effects.

The mineral functional water according to the present invention is characterized by revealing antioxidant effects.

Mineral functional water whose raw material differs from that according to the present invention not to contain sulfur (for example, the mineral functional water disclosed in Reference 3 (Japanese registered patent No. 5864010) does not show significant antioxidant effects.

Why the mineral functional water according to the present invention reveals the antioxidant effects is not clear in some aspects. As mentioned later, the fact that the sulfur is contained as the mineral component therein may be considered as one of the causes.

In this specification, "mineral functional water" means water that contains at least one mineral component to reveal at least one or more kind(s) of beneficial effects.

Furthermore, in this specification, "mineral-containing water" means raw material water at a preceding stage when producing the mineral functional water, and also contains at least one mineral component.

Details thereof will be described regarding a method of producing the mineral functional water according to the present invention.

Note that the mineral-containing water itself may have the beneficial effects, or may not.

In this specification, the "mineral component" does not mean one of inorganic components, which include trace elements, defined in a narrow sense except the 4 Elements of carbon, hydrogen, nitrogen, and oxygen.

As long as co-existing with the inorganic components, the "mineral component" may contain at least one of the 4 Elements of carbon, hydrogen, nitrogen, and oxygen which are excluded in a narrow sense.

Therefore, for example, a "mineral component derived from plants" is a broad concept that includes not only at least one of inorganic components such as calcium derived from the plants but also at least one of organic components other than the above derived from the plants.

The inorganic component constituting the mineral component may be sodium, potassium, calcium, magnesium, phosphorus, or the like. And, the trace element may be iron, zinc, copper, manganese, iodine, selenium, chromium, molybdenum, or the like. However, neither the inorganic component nor the trace element is limited to these elements.

Hereinafter, the mineral functional water according to the present invention will now be explained in more detail.

The words of "antioxidant effects" of the mineral functional water according to the present invention mean the action of scavenging active oxygen and/or free radicals.

The words of "active oxygen" in this specification mean superoxide, hydrogen peroxide, hydroxy radicals, singlet oxygen, or the like.

The words of "free radicals" mean molecules and/or atoms having one or more unpaired electrons. It should be understood, in this specification, that the free radicals means substances other than the active oxygen.

The kinds of free radicals are not limited in particular. For example, 1,1-diphenyl-2-picrylhydrazyl (DPPH) or the like may be adduced related thereto.

As shown in Examples later, the mineral functional water according to the present has antioxidant effects not less than that of vitamin C.

For this reason, the mineral functional water according to the present invention can be used as prophylactic therapeutic agent for diseases caused by active oxygen and/or free radicals.

The words of "diseases caused by active oxygen and/or free radicals" are not limited as long as the diseases may appear, get worse, or develop as the active oxygen and/or free radicals increase(s).

The diseases may be, for example, cardiovascular diseases (aging of blood, arteriosclerosis, myocardial infarction, apoplexy, cerebral infarction, or the like.), internal medicine diseases (cancer, diabetes (cataracts), hepatitis, nephritis, gastric ulcers, intestinal ulcers, decline or absence of sexual desire, or the like.), skin diseases (atopic dermatitis, flecks, wrinkles, rough skin, or the like.), and intractable diseases (collagen diseases, Parkinson's diseases, Behcet's diseases, Kawasaki diseases, articular rheumatism, Raynaud's diseases, or the like.).

There are also some reports reciting that the active oxygen and/or free radicals may cause stiff shoulders, asthenopia, damaged hair (deterioration of hair mother cells, cuticles, scalps, or the like.), and proliferation of acne bacteria. Accordingly, the mineral functional water may be used as prophylactic therapeutic agent for the above.

The mineral functional water according to the present invention performs at least one of superoxide-scavenging action by singlet oxygen, hydrogen peroxide-scavenging, and radical-scavenging action, thereby preventing and/or ameliorating in-vivo oxidation and/or aging of skin.

How to evaluate the superoxide-scavenging action by singlet oxygen, the hydrogen peroxide-scavenging, and the radical-scavenging action is not limited in particular. In other words, the evaluation can be made by means of a conventional method.

For example, for the evaluation of the superoxide-scavenging action, absorption photometry, a chemical fermentation method or the like can be adduced, other than the electron spin resonance spectrum (ESR) method as recited later in Examples.

Why the mineral functional water according to the present invention reveals the antioxidant effects is not clear in some aspects. It may be considered that mineral components containing at least sulfur contribute thereto.

The mineral functional water according to the present invention contains sulfur components as mineral components so as to be designed to irradiate electromagnetic waves (about 3 [THz]) having about 100 micrometers of wavelength.

The design causes activation by resonating with stretching vibration and deformation vibration between sulfur molecules composing cysteine amino acid and their partners of hydrogen.

For this reason, when the mineral functional water according to the present invention (and/or composition containing the same) is orally administered and/or is used while contacting with skin, enzymes including cysteine which is amino acid containing sulfur molecules can be activated.

Therefore, superoxide dismutase (SOD) is activated. So, in addition to the above-mentioned antioxidative activity originally possessed by the mineral functional water according to the present invention, the action of the SOD can synergistically reduce concentration of active oxygen.

Physical functions are activated together with anti-oxidant action, and immune functions are also improved synergistically.

The mineral functional water according to the present invention possesses properties that have excellent safety for both human and animals, and has no toxicity which conventional disinfectant possesses to cause no problem when it is sucked and/or adhered to skin. Accordingly, protective tools, such as a rubber glove, a goggle, and a mask are not needed.

The mineral functional water according to the present invention may be diluted with preferable dilute solvents (water, alcohol, or the like) within a range wherein the object according to the present invention is not spoiled.

Optional components may be contained in the mineral functional water according to the present invention within a range wherein the effects thereof is not spoiled.

The optional components are not limited within the range wherein the object according to the present invention is not spoiled. Known suspension, emulsion, or the like may be used, for example.

A mixing ratio thereof is optional within the range wherein the object according to the present invention is not spoiled.

The mineral functional water according to the present invention may be used as it is. Alternatively, it may be condensed to be used upon being used as active ingredients of composition.

<2 Usage of Mineral Functional Water>

The mineral functional water according to the present invention has one or more items of beneficial effects.

Hereinafter, usage based on the anti-oxidant action which is one of items of beneficial effects according to the present invention will now be explained.

The mineral functional water according to the present invention hardly has toxicity and irritation to human bodies.

For this reason, the water can be used while being directly contacted with human skin.

Because of possessing anti-oxidant action, the mineral functional water according to the present invention can be used as active ingredients of antioxidation composition.

Based on the anti-oxidant action the water has active oxygen-scavenging action and/or radical-scavenging action. So, the water can be also used as active ingredients of oxygen-scavenging composition and/or radical-scavenging composition.

The mineral functional water according to the present invention possesses anti-oxidant action. So, adding the water to the objects of food, drinks, cosmetics, medicines, or the like enables to prevent components (oil, fats, or the like.) contained in the objects from being oxidized and/or deteriorated caused by active oxygen and/or free radicals.

The mineral functional water according to the present invention possesses anti-oxidant action. So, taking the water enables to effectively prevent and/or ameliorate symptoms, signs, and diseases caused by increasing active oxygen and/or free radicals. The diseases may be cold, articular rheumatism, arteriosclerosis, diabetes, nephritis, stiff shoulders, and so on.

The mineral functional water according to the present invention contains sulfur components as mineral components so as to be designed to resonate with stretching vibration and deformation vibration between sulfur atoms of cysteine composing cysteine amino acid and their partners of hydrogen.

Therefore, superoxide dismutase (SOD) is activated. So, together with the above-mentioned antioxidative activity, concentration of active oxygen is reduced.

That is, it can be said that the mineral functional water according to the present invention has superoxide dismutase (SOD)-like action.

Physical functions are activated together with anti-oxidant action, and immune functions are also improved synergistically. Due to this, healthy constitution strong against oxidative stress can be made.

In many cases, skin aging phenomena such as wrinkles, sagging, rough skin, or the like may be caused by active oxygen and/or free radicals. The antioxidant effects of the mineral functional water according to the present invention can contribute to prevent and/or ameliorate the skin aging phenomena including abnormal generation of melanin, wrinkles, sagging, rough skin, or the like.

One or more arbitrary components may be added to the mineral functional water according to the present invention to produce composition thereof.

Components other than the mineral functional water of composition containing the mineral functional water according to the present invention as active ingredients can be selected taking the usage thereof into consideration.

Also mixing ratio thereof may also be suitably chosen according to the usage.

[3. Method of Producing Mineral Functional Water According to the Present Invention]

A method of producing the mineral functional water containing mineral components radiating electromagnetic waves (hereinafter, may be called as "the mineral functional water according to the present invention") is not specially limited, which can be, utilizing the producing apparatus disclosed in Reference 2 (Japanese patent application Laid-open No. 2011-56366), produced according to a method based on the methods disclosed therein.

As long as capable of obtaining the mineral functional water containing mineral components radiating electromagnetic waves, a method of producing the same is not limited to the above method utilizing the producing apparatus, and another method may be used instead thereof.

Hereinafter, referring to the attached drawings, preferable Embodiment related to a method of producing mineral functional water according to the present invention utilizing the apparatus disclosed in Reference 2 (Japanese patent application Laid-open No. 2011-56366) will now be explained.

As shown in FIG. 1, mineral functional water-producing equipment 1 includes: the mineral-containing water (A) producing apparatus 2; the mineral-containing water (B) producing apparatus 3; and the mixing tank 46 which is a mixing unit for mixing mineral-containing water (A) 44 produced by the mineral-containing water (A) producing apparatus 2 with mineral-containing water (B) 45 produced by the mineral-containing water (B) producing apparatus 3 to form mineral functional water 47.

Figure 4:
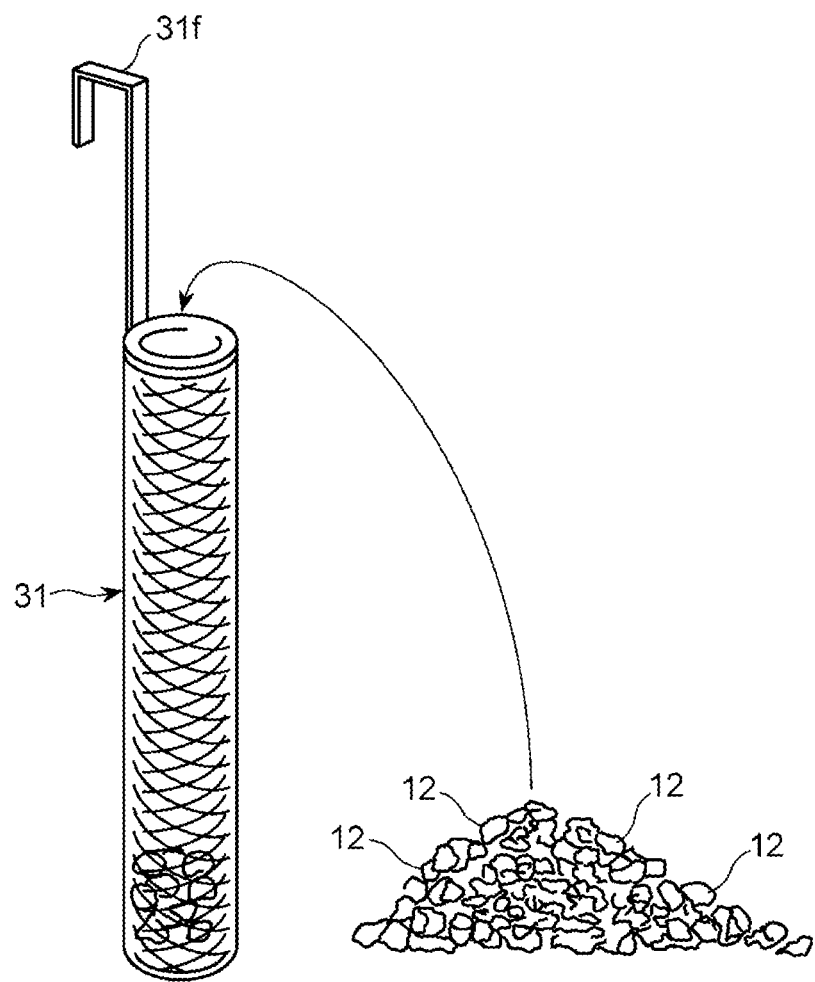
FIG. 4 is a perspective view of a housing container of the mineral-imparting material (A) used for the raw mineral water solution production unit shown in FIG. 2.

The mineral-containing water (A) producing apparatus 2 includes: the raw mineral water solution production unit 10 using raw material of water 11 supplied from waterworks and mineral-imparting material (A) 12 mentioned later (See, FIG. 4.) to form raw mineral water solution (A) 41; and an far-infrared ray-generating unit 43 irradiating far-infrared rays to the raw mineral water solution (A) 41 obtained by the raw mineral water solution production unit 10 to change the raw mineral water solution (A) 41 into mineral-containing water (A) 44.

The mineral-containing water (B) producing apparatus 3 has a function of forming the mineral-containing water (B) 45 containing mineral components eluted from mineral-imparting material by making water W supplied from the outside pass through the water-passing containers 51-56.

Hereinafter, details of the mineral-containing water (A) producing apparatus 2 and the mineral-containing water (B) producing apparatus 3 will now be explained.

(3-1: Mineral-Containing Water (A) Producing Apparatus)

Next, referring to FIG. 2-FIG. 6, the mineral-containing water (A) producing apparatus 2 constituting the mineral functional water-producing equipment 1 shown in FIG. 1 is explained.

As shown in FIG. 1, the mineral-containing water (A) producing apparatus 2 includes: the raw mineral water solution production unit 10 (See, FIG. 2) using raw material of water 11 supplied from waterworks and mineral-imparting material (A) 12 mentioned later (See, FIG. 4) to form raw mineral water solution (A) 41; and the far-infrared ray-generating unit 43 (See, FIG. 6) irradiating far-infrared rays to the mineral-containing water (A) solution 41 obtained by the raw mineral water solution production unit 10 to change the mineral-containing water (A) solution 41 into the mineral-containing water (A) 44.

Figure 2:
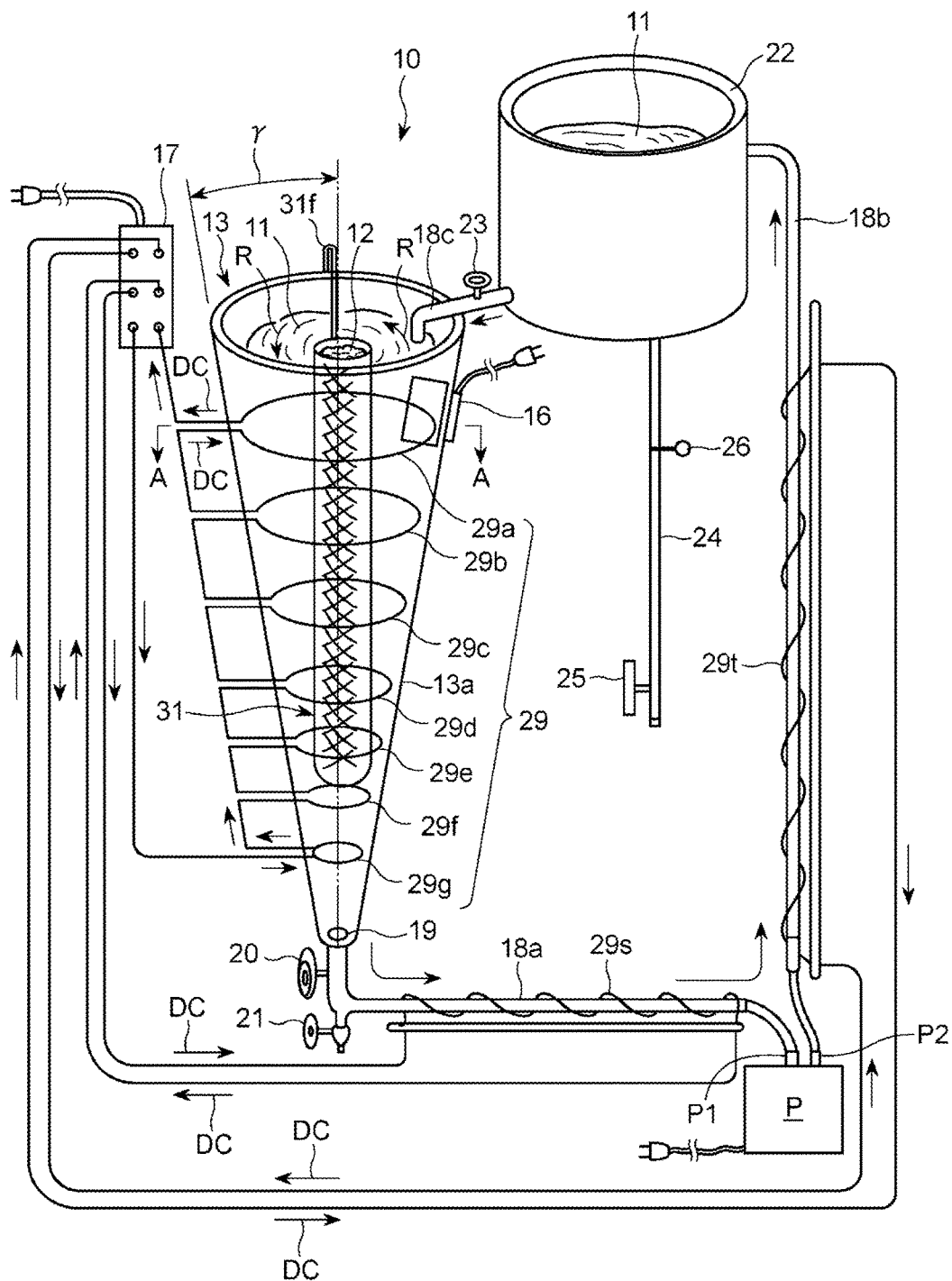
FIG. 2 is a mimetic diagram of a mineral-containing water solution production unit configuring a part of mineral-containing water (A) producing apparatus that constitutes the mineral functional water-producing equipment shown in FIG. 1.
Figure 3:
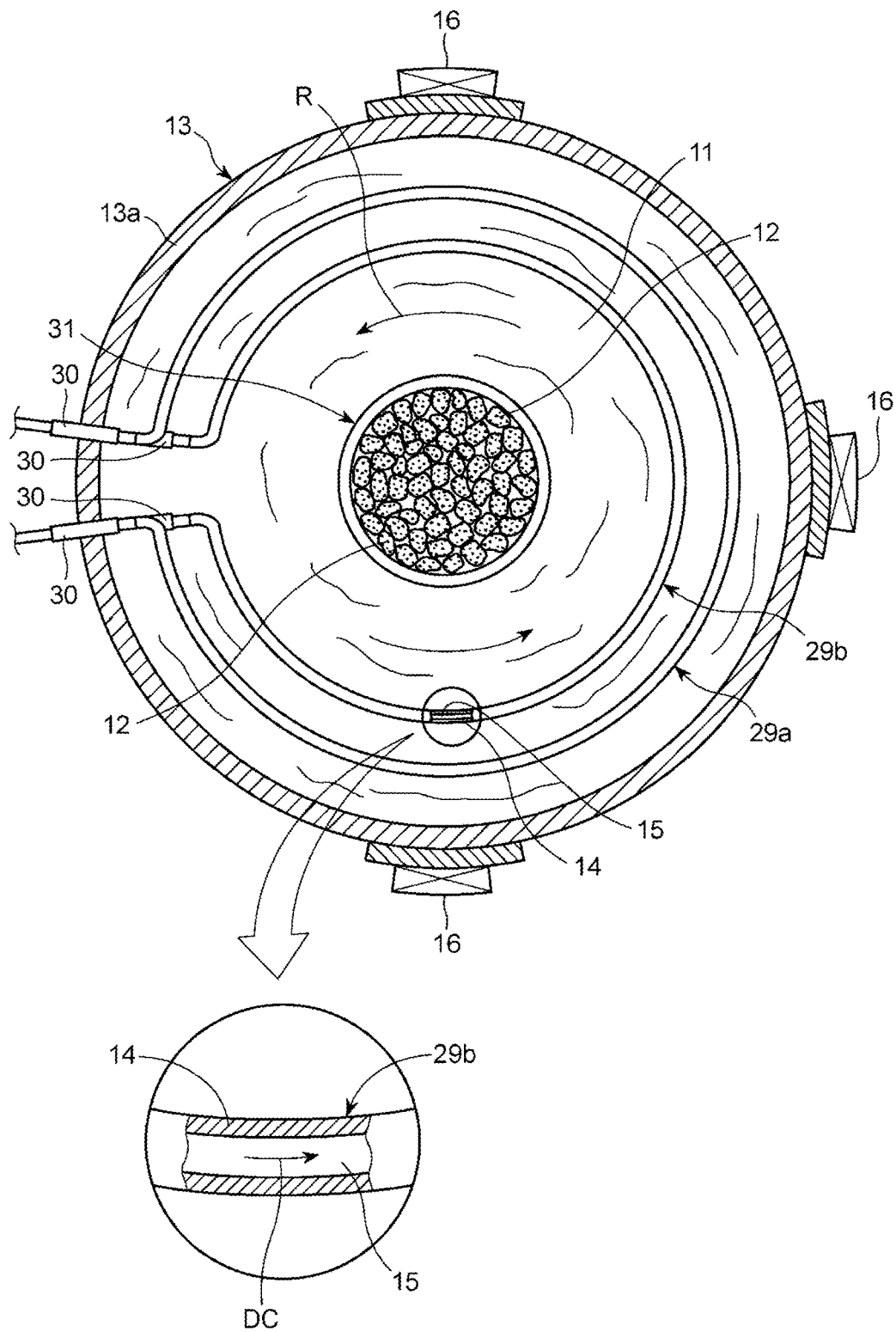
FIG. 3 is a partial sectional view of FIG. 2 according to the A-A line thereof.

As shown in FIG. 2 and FIG. 3, the raw mineral water solution production unit 10 includes: a reaction vessel 13 capable of storing the water 11 and the mineral-imparting material (A) 12 therein; the conductive wire 15 covered with the insulator 14 and immersed into the water 11 of the reaction vessel 13; the ultrasonic wave generation unit 16 applying ultrasonic vibration onto the water 11 in the reaction vessel 13; the DC power supply device 17 conducting DC electric current to the conductive wire 15; the circulating passages 18a and 18b which are means for generating the water flow R around the conductive wire 15 in the same direction as that of the DC electric current; and the circulation pump P.

Each of the DC power supply device 17, the ultrasonic wave generation unit 16, and the circulation pump P operates using electric supply from general commercial power.

The reaction vessel 13 is formed in a shape of an inverted conical whose upper surface is opened, and the drain port 19 is provided with a bottom thereof corresponding to the lower summit of the conical.

The circulating passage 18a communicating with the suction port P1 of the circulation pump P is connected to this drain port 19. The opening control valve 20 for adjusting volume of wastewater to the circulating passage 18a and the drain valve 21 for discharging the water or the like in the reaction vessel 13, are provided directly under the drain port 19.

A proximal end of the circulating passage 18b is connected to the discharge port P2 of circulation pump P, and a distal end of the circulating passage 18b is connected to the housing tank 22.

A proximal end of the circulating passage 18c for transporting the water 11 in the housing tank 22 into the reaction vessel 13 is connected near a bottom portion on the outer periphery of the housing tank 22, and a distal end of the circulating passage 18c is piped at a position facing an opening portion of the reaction vessel 13.

The opening control valve 23 for adjusting an amount of water transported into the reaction vessel 13 from the housing tank 22 is provided with the circulating passage 18c.

The drain pipe 24 including: the drain valve 25; and the water temperature gage 26, is connected to a bottom portion of the housing tank 22 in a suspended state.

If needed, upon opening the drain valve 25, the water in housing tank 22 can be discharged from a bottom end of the drain pipe 24, and at this time temperature of the water 11 passing through the drain pipe 24 can be measured with the water temperature gage 26.

Figure 5:
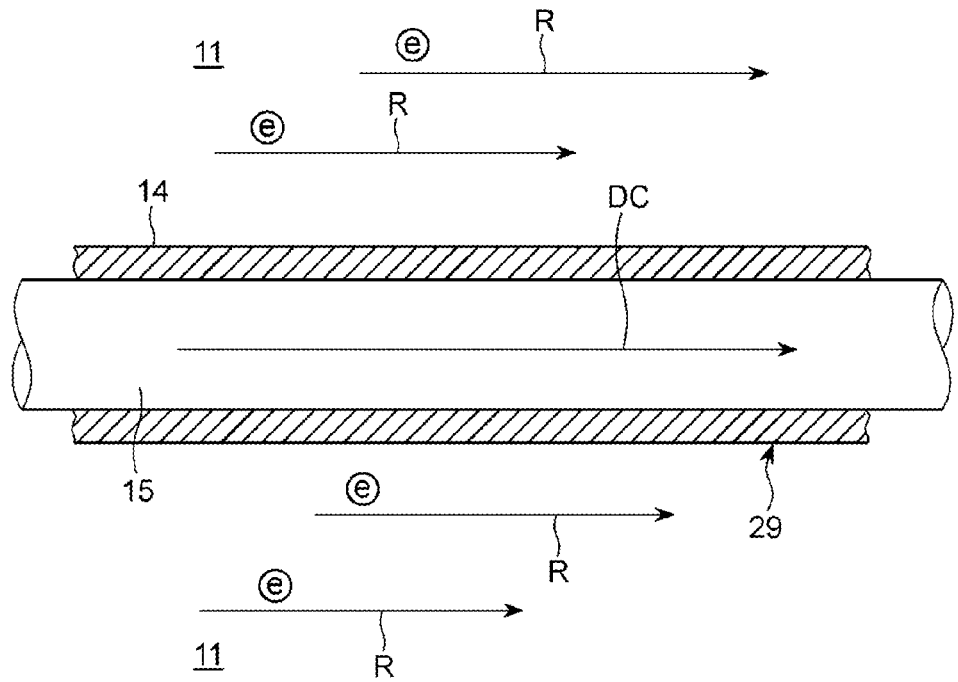
FIG. 5 is a mimetic diagram showing a reaction state near a conductive wire in the raw mineral water solution production unit shown in FIG. 2.

As shown in FIG. 5, the plurality of conductive cables 29 (29a-29g) each of which includes: the conductive wire 15; and the insulator 14 covering the wire are wired so as to have shapes of rings located at positions having different depth from each other in the reaction vessel 13, respectively. All of the plurality of conductive cables 29a-29g and the reaction vessel 13 are coaxially arranged.

According to inside diameters of the reaction vessel 13 in the shape of the inverted conical, inside diameters of the plurality of conductive cables 29a-29g are gradually contracted so as to be a diameter corresponding to the respective arranged position thereof.

Each of the plurality of conductive cables 29a-29g is detachably connected to the insulating terminal 30 provided with the wall body 13a of the reaction vessel 13, if needed, a circular portion of the cables may be detached from the terminal 30, or may be attached thereto.

The cylindrical housing container 31 having a bottom portion and being formed with an insulating reticulum, is arranged at a portion corresponding an axial center of the reaction vessel 13. And, the mineral-imparting material (A) 12 is filled up within the housing container 31.

This housing container 31 is, by the hook 31f provided with an upper portion thereof, detachably engaged with an upper edge portion of the wall body 13a of the reaction vessel 13.

As shown in FIG. 2, the conductive cables 29s and 29t are spirally twisted around the periphery of the circulating passages 18a and 18b, respectively. DC electric current is supplied from the DC power supply device 17 to these conductive cables 29s and 29t.

A direction in which the DC electric current flows through the conductive cables 29s and 29t is set up so as to meet a direction in which the water flow runs within the circulating passages 18a and 18b.

In the raw mineral water solution production unit 10, a predetermined amount of water 11 is put into the reaction vessel 13 and the housing tank 22.

After having set the housing container 31, into which the mineral-imparting material (A) 12 has been filled up, to a center of the reaction vessel 13, the circulation pump P is activated, and the opening control valve 20 provided with the bottom portion of the reaction vessel 13 and the opening control valve 23 of the circulating passage 18c are adjusted.

Next, the water 11 from the reaction vessel 13 is made circulate so as to pass through the drain port 19, the circulating passage 18a, the circulation pump P, the circulating passage 18b, the housing tank 22, and the circulating passage 18c, thereby returning to the upper portion of the reaction vessel 13 again.

And then, upon activating the DC power supply device 17 and the ultrasonic wave generation unit 16, the elution reaction of the mineral components from the mineral-imparting material (A) 12 in the housing container 31 to the water 11 begins.

The working conditions when producing the raw mineral water solution (A) using the raw mineral water solution production unit 10 are not limited in particular. In this Embodiment, however, the raw mineral water solution (A) has been produced according to the following working conditions.

(1) The DC electric current DC having voltage of 8000-8600 V and current of 0.05-0.1 A has been conducted through the conductive cables 29, 29s, and 29t.

The insulator 14 constituting the conductive cable 29 or the like is made of polytetrafluoroethylene resin.

(2) The mineral-imparting material (A) 12 is filled up in the reaction vessel 13 with a mass ratio of 10 to 15% based on the water 11.

The mineral-imparting material (A) 12 will be explained later referring to concrete examples.

(3) It is sufficient that the water 11 merely contain electrolyte so that the DC electric current can work therethrough.

For example, when containing about 10 g of sodium carbonates, which is a kind of electrolyte, based on 100 liters of the water, the water may be used as the water 11. Alternatively, groundwater, as it is, can be used as the water 11.

(4) The ultrasonic wave generation unit 16 generates ultrasonic waves having a frequency of 30-100 kHz, and is arranged so that an ultrasonic vibration portion (not shown) thereof directly contact with the water 11 in the reaction vessel 13 to make the water 11 vibrate.

When the raw mineral water solution production unit 10 is activated on such conditions, in the reaction vessel 13, the water flow R rotating in a direction of a left-hand thread and being sucked into the drain port 19 occurs, the water 11 discharged from the drain port 19 passes through the circulating passages 18a and 18b or the like, and returns again into the reaction vessel 13. This state is continued.

Therefore, agitating action by the water flow R, action of the direct electric current flowing through the conductive cable 29, and ultrasonic vibration generated by the ultrasonic wave generation unit 16, make mineral components speedily elute from the raw mineral water solution (A) into the water 11, thereby enabling to produce with high efficiency the mineral-imparting material (A) 12 that necessary mineral components have been moderately dissolved therein.

In the raw mineral water solution production unit 10, the plurality of conductive cables 29a-29g, each of which is formed in the shape of the ring, are coaxially arranged within the reaction vessel 13. The water flow R rotating in the direction of the left-hand thread within the reaction vessel 13 is also generated.

Due to this, a comparatively dense field of electrical energy can be formed within the reaction vessel 13 of fixed volume. In other words, the raw mineral water solution (A) can be efficiently produced within the reaction vessel 13 having comparatively small capacity.

The reaction vessel 13 is formed in the shape of the inverted conical. Therefore, the water flow R flowing along with the plurality of conductive cables 29a-29g in the shapes of the rings can be generated comparatively easily and stably, thereby promoting elution of the mineral components.

The water flow R flowing in the inside of reaction vessel 13 shaped of the inverted conical increases flow velocity thereof as it goes toward the drain port 19 at the bottom portion of the reaction vessel 13. Therefore, contact frequency with the mineral-imparting material (A) 12 can also increase so as to catch more free electrons e existing in the water 11, thereby capable of increasing an amount of ionized minerals.

Furthermore, the housing tank 22 discharging and storing water 11 is provided between the circulating passages 18b and 18c. Therefore, while circulating the water 11 whose amount is greater than the volume of the reaction vessel 13, elution action of minerals can proceed.

For this reason, the raw mineral water solution (A) can be mass-produced with remarkably high efficiency.

When the circulation pump P is made continuously run to continue the above action, the raw mineral water solution (A) in which the mineral components have been eluted is produced as a result.

According to conditions including: the size of the drain port 19 at the bottom portion of the reaction vessel 13; the amount of circulating water; the shape (especially, the angle γ shown in FIG. 2 between the axial center C and the wall body 13a) of the reaction vessel 13; and so on, the appearance situation of free electrons e in the water 11 can be controlled. Action of the free electrons e upon the mineral-imparting material (A) 12 may change the water solubility of the mineral components.

Figure 6:
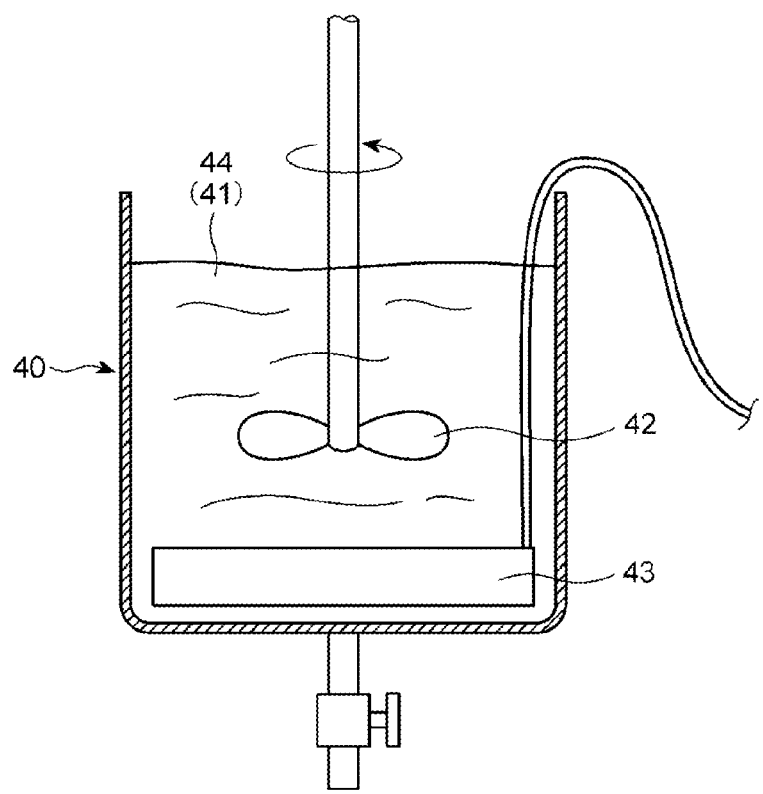
FIG. 6 is a sectional view of far-infrared ray-irradiating apparatus configuring a part of the mineral-containing water (A) producing apparatus that constitutes the mineral functional water-producing equipment shown in FIG. 1.

When the raw mineral water solution (A) has been formed, this raw mineral water solution (A) 41 is moved into the treatment container 40 shown in FIG. 6.

At this stage, the residue of the mineral-imparting material (A) 12 leaked from the housing container 31 in the reaction vessel 13 can be discharged from the drain valve 21 at the bottom portion of the reaction vessel 13.

The far-infrared ray-generating unit 43 arranged within the treatment container 40 irradiates far-infrared rays to the raw mineral water solution (A) 41 stored in the treatment container 40 while the raw mineral water solution (A) 41 is slowly agitated by the agitation blades 42.

It is sufficient for the far-infrared ray-generating unit 43 to generate far-infrared rays with wavelength of about 6-14 micrometers. The material and/or the generating unit thereof may be optional, and a heating method may be used for the same.

However, it is preferable that the unit has, at 25 Centigrade, emissivity of 85% or more to the radiation of the black body within a band of 6-14 micrometer wavelength.

In the raw mineral water solution production unit 10 shown in FIG. 2, according to: the agitation action by the water flow R; the action by the DC electric current conducting through the conductive wire 15; and the ultrasonic vibration, the mineral components contained in the mineral-imparting material (A) 12 speedily elutes into the water 11, thereby enabling to produce the mineral water solution 41 in which necessary mineral components have been moderately melt with high efficiency.

The far-infrared ray-generating unit 43 shown in FIG. 6 irradiates far-infrared rays to the mineral water solution 41 to amalgamate dissolved mineral components with water molecules, thereby producing the mineral-containing water (A) 44 whose electro-negativity is increased.

As shown in FIG. 1, the mineral-containing water (A) 44 formed according to the above-mentioned processes in the mineral-containing water (A) producing apparatus 2 is transported into the mixing tank 46 via the water supply passage 57y, and is mixed with the mineral-containing water (B) 45 transported from the mineral-containing water (B) producing apparatus 3 within the mixing tank 46.

Hereinafter, the mineral-imparting material (A) will now be explained.

The mineral-imparting material (A) contains: the vegetation raw material including at least one kind selected from a group consisting of vegetation belonging to Asteraceae, and vegetation belonging to Rosaceae; the woody plant raw material of woody plants including at least one kind selected form a group consisting of *Maple*, *Betula platyphylla*, *Pinus*, and *Cryptomeria japonica*, and sulfur raw material.

Vegetation other than Asteraceae and Rosaceae may be included. However, it is preferable that the only vegetation belonging to Asteraceae and Rosaceae is used.

As preferable Asteraceae vegetation, *Farfugium japonicum*, *Artemisia indica*, *Cirsium japonicum*, or the like are adduced.

As preferable Rosaceae vegetation, *Rosa multiflora*, *Geum japonicum*, *Potentilla hebiichigo*, *Kerria japonica*, *Rubus* L., or the like are adduced.

Used parts of the vegetation may be selected from a group from which mineral components are easily eluted, the group including leaf parts, stem parts, and flower parts. The used parts may be used as they are. Dried product therefrom may be used instead.

As the woody plant, *Maple*, *Betula platyphylla*, *Pinus*, and *Cryptomeria japonica* are adduced.

Used parts of the woody plant may be selected from a group from which mineral components are easily eluted, the group including leaf parts, stem parts, and flower parts. The used parts may be used as they are. Dried product therefrom may be used instead.

The followings are preferable. That is, dried pulverized product of Asteraceae plants and dried pulverized product of Rosaceae plants are used as the mineral-imparting material (A);

the dried pulverized product of the Asteraceae plants is produced by: mixing 10 weight % of *Cirsium japonicum* (leaf parts, stem parts and flower parts thereof), 60 weight % of *Artemisia indica* (leaf parts and stem parts thereof) and 30 weight % of *Farfugium japonicum* (leaf parts and stem parts thereof), respectively to produce first mixture thereof; making the first mixture dry; and then pulverizing the dried first mixture;

the dried pulverized product of the Rosaceae plants is produced by:

mixing 20 weight % of *Rosa multijiora* (leaf parts and flower parts thereof), 10 weight % of *Geum japonicum* (leaf parts and stem parts thereof), and 70 weight % of *Rubus* L. (leaf parts, stem parts, and flower parts thereof), respectively to produce second mixture thereof; making the second mixture dry; and then pulverizing the dried second mixture;

the dried pulverized product of the Asteraceac plants and the dried pulverized product of the Rosaceae plants are mixed according to 1:1 (weight ratio) to obtain vegetation raw material (A1);

the woody plant raw material (A2) is produced by:

mixing 20 weight % of *Maple* (fallen leaf parts and stem parts thereof), 60 weight % of *Betula platyphylla* (fallen leaf parts, stem parts, and bark parts thereof), and 20 weight % of *Cryptomeria japonica* (fallen leaf parts, stem parts, and bark parts thereof) to produce third mixture; making the third mixture dry; and then pulverizing the dried third mixture; and the sulfur raw material is composed of volcanic sulfur (A3); and mineral-imparting material (A') is obtained by:

mixing the vegetation raw material (A1) and the woody plant raw material (A2) according to 1:5 (weight ratio) to produce plant mixture; and based on 100 pts.wt. of the plant mixture, mixing 2-8 weight % of the volcanic sulfur (A3).

Herein, the volcanic sulfur (A3) is sulfur-containing substances existing in volcanoes.

It is sufficient that the volcanic sulfur (A3) is dissolved and/or distributed upon communicating with water, thereby sulfur components therefrom are dissolved into the mineral-containing water (A). The volcanic sulfur (A3) is preferable because it has a feature of making anti-inflammatory activities and/or antioxidant effects special to the mineral functional water according to the present invention exhibit stronger.

As the volcanic sulfur (A3), powder produced by having shattered the sulfur-containing substances is preferably used.

Based on 100 pts. wt. of mixture produced by mixing the vegetation raw material (A1) and the woody plant raw material (A2) according to a weight ratio of 1:5, the volcanic sulfur (A3) is added thereto within a range of 2 through 8 pts. wt.

As the vegetation raw material (A1), "P-101 (lot number)" produced by Riken techno system Co., LTD. can be used. And, as the woody plant raw material (A2), "P-201 (lot number)" produced by Riken techno system Co., LTD. can be preferably used.

As the volcanic sulfur (A3), "S-100 (lot number)" produced by Riken techno system Co., LTD. can be preferably used.

(3-2: Mineral-Containing Water (B) Producing Apparatus)

Next, referring to FIG. 1 and FIG. 7, the structure and the functions of the mineral-containing water (B) producing apparatus 3, or the like will now be explained.

Figure 7:
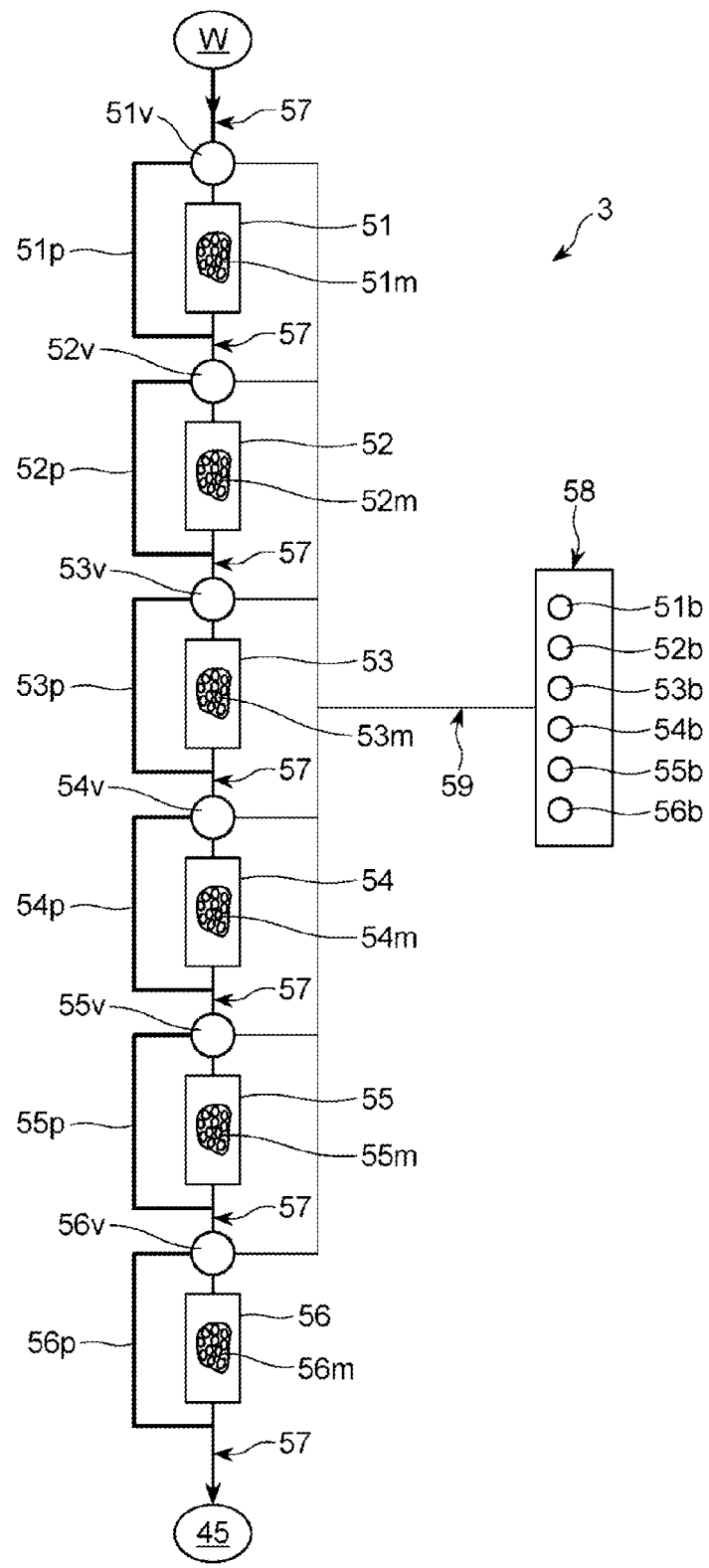
FIG. 7 is a block diagram of mineral-containing water (B) producing apparatus that constitutes the mineral functional water-producing equipment shown in FIG. 1.

As shown in FIG. 1 and FIG. 7, the mineral-containing water (B) producing apparatus 3 includes: the first, the second, the third, the fourth, the fifth, and the sixth water-passing containers 51-56 into which a different kind of mineral-imparting material (B) from each other is filled up, respectively; the water supply passage 57 communicating the plurality of water-passing containers 51-56 in series; and the roundabout channels 51p-56p connected to the water supply passage 57 in a state where the roundabout channel is parallel to the plurality of water-passing containers 51-56, respectively; and the water stream-changing valves 51v-56v provided in branch parts from the water supply passage 57 and the roundabout channels 51p-56p, respectively The operation of switching the water stream-changing valves 51v-56v can be performed by operating the six switching buttons 51b-56b provided on the operation panel 58 connected to these water stream-changing valves 51v-56v via the signal cables 59.

The six switching buttons 51b-56b and the six water stream-changing valves 51v-56v correspond to each other according to the numbers thereof. Upon operating a certain one of the switching buttons 51b-56b, one of the water stream-changing valves 51v-56v having a number corresponding to the certain one is switched to change the direction of a water flow related thereto.

Here, the mineral-imparting material (B) 51m-56m can be preferably produced by mixing raw material based on a lime stone, fossil coral, and shell.

Firstly, components contained in the lime stone, the fossil coral, and the shell is analyzed, and the amounts of silicon dioxide, iron oxide, activated carbon, titanium nitride, calcium carbonate, magnesium carbonate, and calcium phosphate are evaluated, respectively.

Secondly, based on the respective content of the components, the lime stone, the fossil coral, and the shell are mixed to produce the mineral-imparting material (B) 51m-56m.

It is preferable that components contained in the mineral-imparting material (B) 51m-56m is controlled according to the mixing ratio of the lime stone, the fossil coral, and the shell. However, in some cases, the material of the lime stone, the fossil coral, and the shell has poor component(s) according to the source thereof. If so, at least one of silicon dioxide, iron oxide, activated carbon, titanium nitride, calcium carbonate, magnesium carbonate, and calcium phosphate may be added, if needed.

Especially, since the activated carbon is rarely contained in the lime stone, the fossil coral, and the shell, the activated carbon should usually be added separately.

When as the mineral-imparting material (B) 51m-56m, the mineral-imparting material (B1) filled into the first water-passing container 51 is mixture including: 70 weight % of lime stone; 15 weight % of fossil coral; and 15 weight % of shell, respectively; the mineral-imparting material (B2) filled into the second water-passing container 52 is mixture including: 40 weight % of lime stone; 15 weight % of fossil coral; 40 weight % of shell; and 5 weight % of activated carbon, respectively; the mineral-imparting material (B3) filled into the third water-passing container 53 is mixture including: 80 weight % of lime stone; 15 weight % of fossil coral; and 5 weight % of shell, respectively; the mineral-imparting material (B4) filled into the fourth water-passing container 54 is mixture including: 90 weight % of lime stone; 5 weight % of fossil coral; and 5 weight % of shell, respectively; the mineral-imparting material (B5) filled into the fifth water-passing container 55 is mixture including: 80 weight % of lime stone; 10 weight % of fossil coral; and 10 weight % of shell, respectively; and the mineral-imparting material (B6) filled into the sixth water-passing container 56 is mixture including: 60 weight % of lime stone; 30 weight % of fossil coral; and 10 weight % of shell, respectively, the mineral-containing water (B) that shows excellent controlling effects can be obtained upon being mixed with the mineral-containing water (A).

Especially, it is preferable that the lime stones, the fossil coral, and the shell that are used for the mineral-imparting material (B1)-(B6) satisfy the following Items (1-1) to (1-3).

Item (1-1): Lime Stone

The lime stone is a small stone produced by crushing a rock of lime in which volcanic ore deposits containing the following components are mixed into a size of about 3 cm:
  calcium carbonate: 50 weight % or more;
  iron oxide: 3 to 9 weight % of iron; and
  sum total of titanium oxide, titanium carbide, titanium nitride: 0.8 weight % or more, and
  magnesium carbonate: 7 to 10 weight %.

"CC-200 (lot number)" produced by Riken techno system Co., LTD. can be preferably used as such a lime stone.

(1-2) Fossil Coral:

The fossil coral is granular material produced by mixing the following the two kinds of raw fossil coral according to a weight ratio of 1:9 to form mixture, and crushing the mixture into the size within 3-5 mm, the two kinds of raw fossil coral including:
  first fossil coral produced about 100 meters below the ground whose crystal construction has been denatured by pressure; and
  second fossil coral produced from land near Amami-ohshima Island, Okinawa-Ken, Japan, and including: calcium carbonate; calcium phosphate; and other trace elements.

As such fossil coral, "CC-300 (lot number)" produced by Riken techno system Co., LTD. can be preferably used.

(1-3) Shell:

The shell is granular material produced by mixing ear shell, abalone, and acorn shell of the same weight to form mixture, and crushing the mixture into the size within 3-5 mm.

"CC-400 (lot number)" produced by Riken techno system Co., LTD. can be preferably used as such shell.

(1-4) Activated Carbon

The activated carbon may be made of optional material. However, preferably, activated carbon made of coconut shell can be adduced.

For example, "CC-500 (lot number)" produced by Ripen techno system Co., LTD. whose raw material is coconut shell made in Thailand can be adduced.

Upon operating the switching buttons 51b-56b on the operation panel 58 mentioned above to switch the water stream-changing valves 51v-56v to the water-passing container side, water having passed through water supply passage 57 flows in into the first water-passing container 51 through the sixth water-passing container 56 located at the downstream of the operated water stream-changing valves. Alternatively, upon switching the water stream-changing valves 51v-56v to the roundabout channel side, the water having passed through water supply passage 57 flows into the roundabout channels 51p-56p located at the downstream of the operated water stream-changing valves.

Therefore, operating any of the switching buttons 51b-56b to selectively change the water stream-changing valves 51v-56v enables to produce the mineral-containing water (B) 45 into which mineral components selectively eluted from the mineral-imparting material (B) 51m-56m whose mineral components differ from each other according to the first water-passing container 51 through the sixth water-passing container 56.

Next, referring to FIG. 8 through FIG. 11, the practical structure and functions of the mineral-containing water (B) producing apparatus 3 will now be explained.

Figure 8:
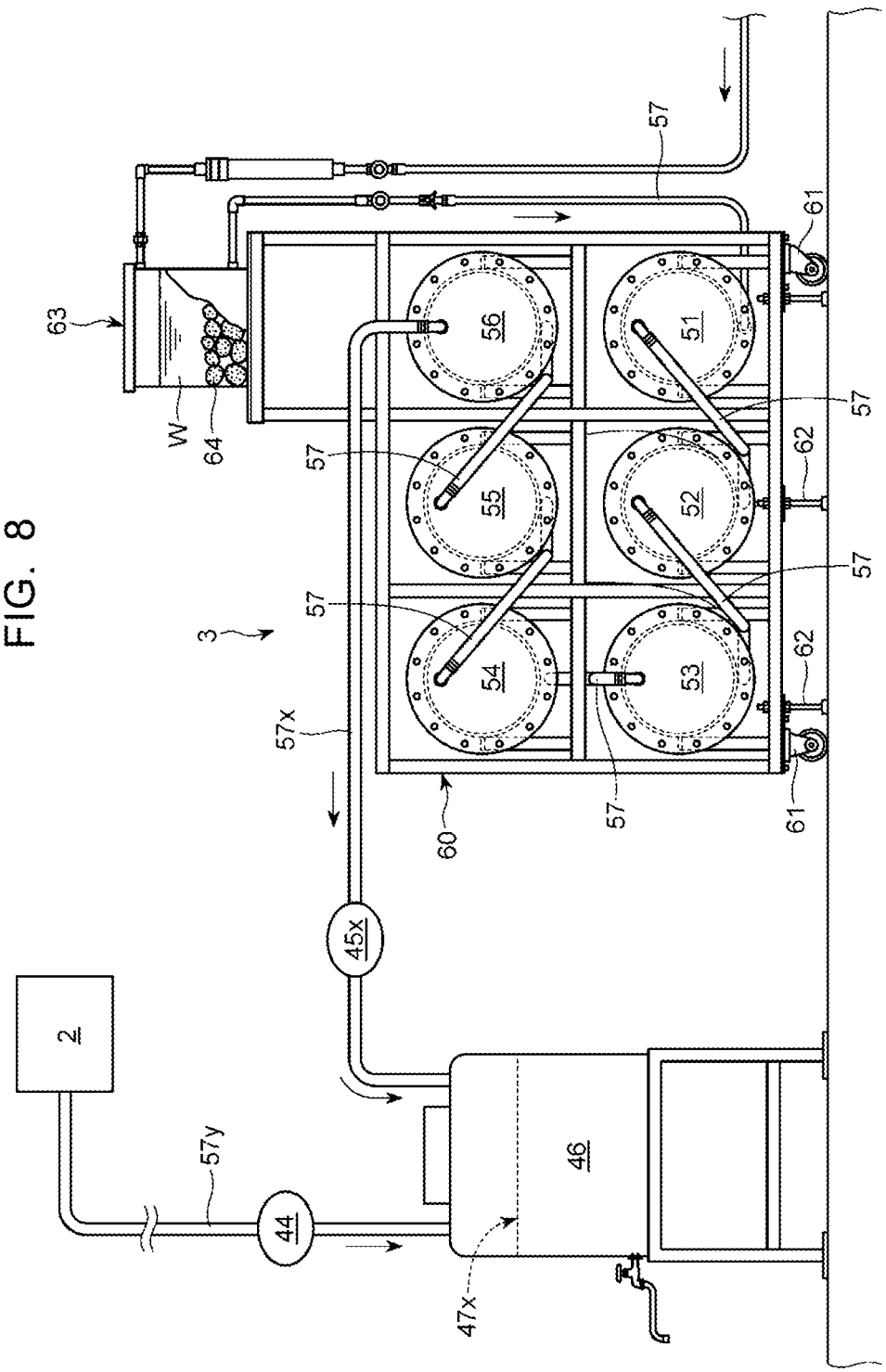
FIG. 8 is a front view showing the mineral-containing water (B) producing apparatus that constitutes the mineral functional water-producing equipment shown in FIG. 1.
Figure 9:
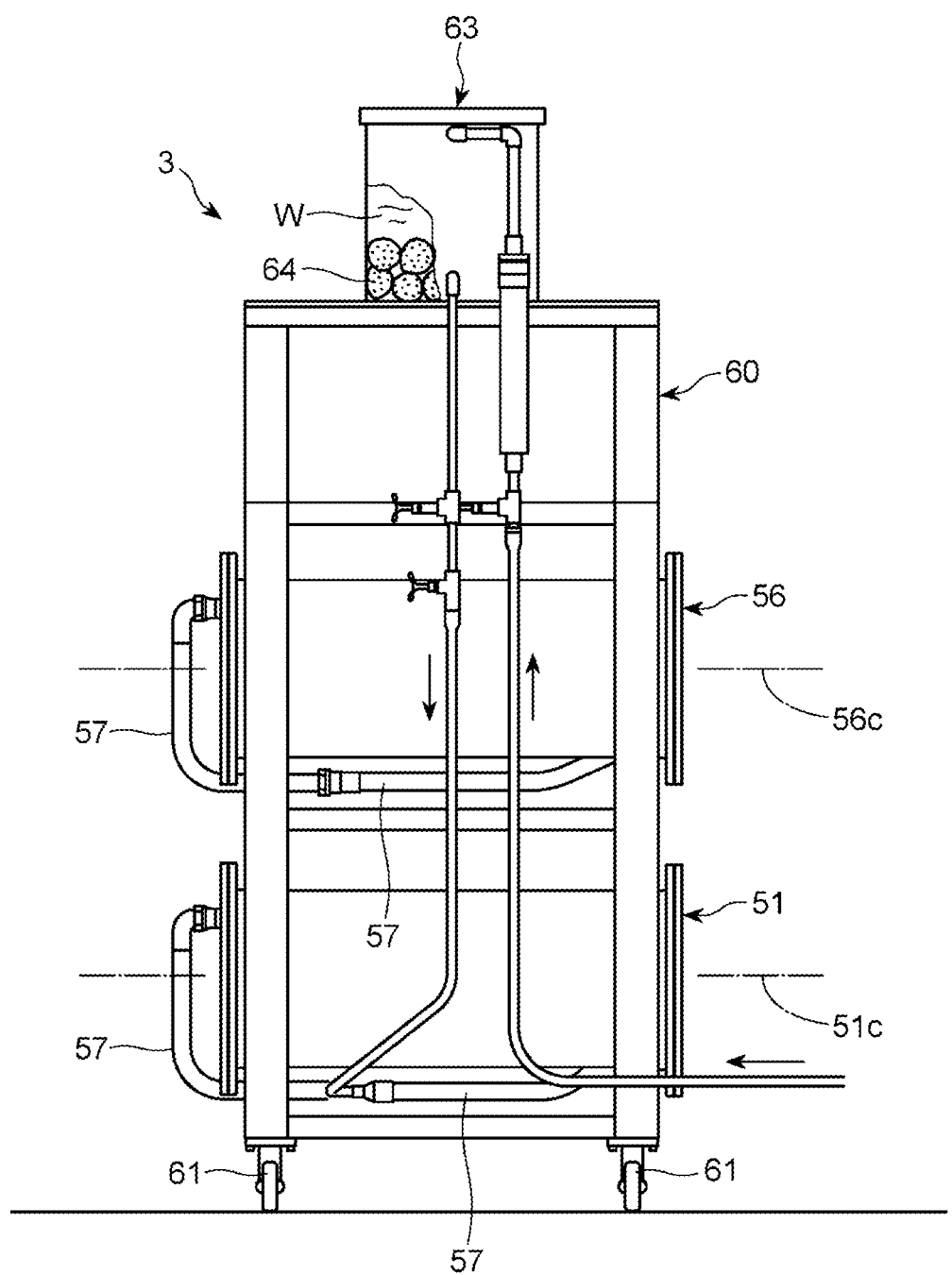
FIG. 9 is a side view of the mineral-containing water (B) producing apparatus shown in FIG. 8.
Figure 10:
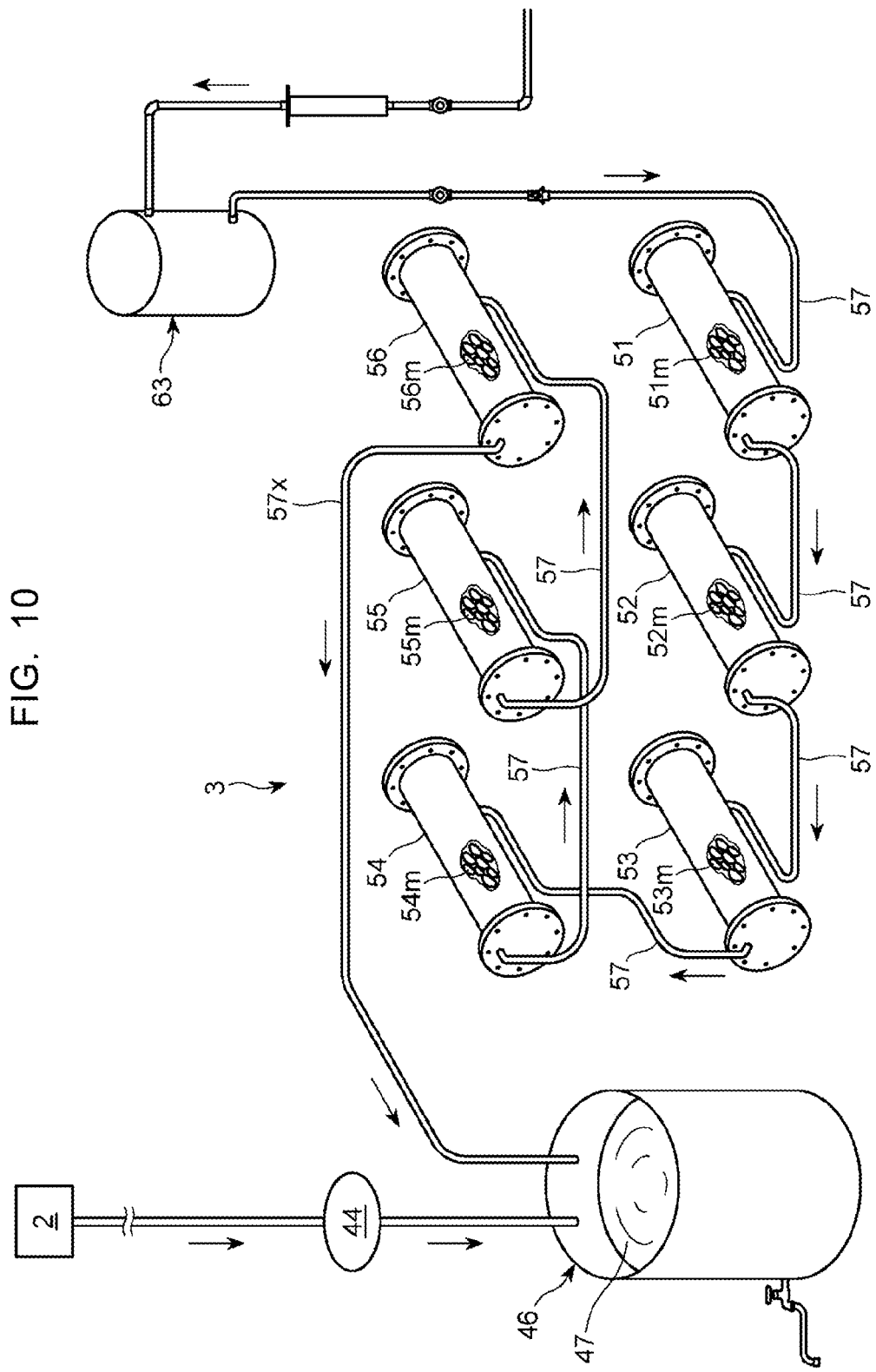
FIG. 10 is a partial perspective view showing the structure of the mineral-containing water (B) producing apparatus shown in FIG. 8.
Figure 11:
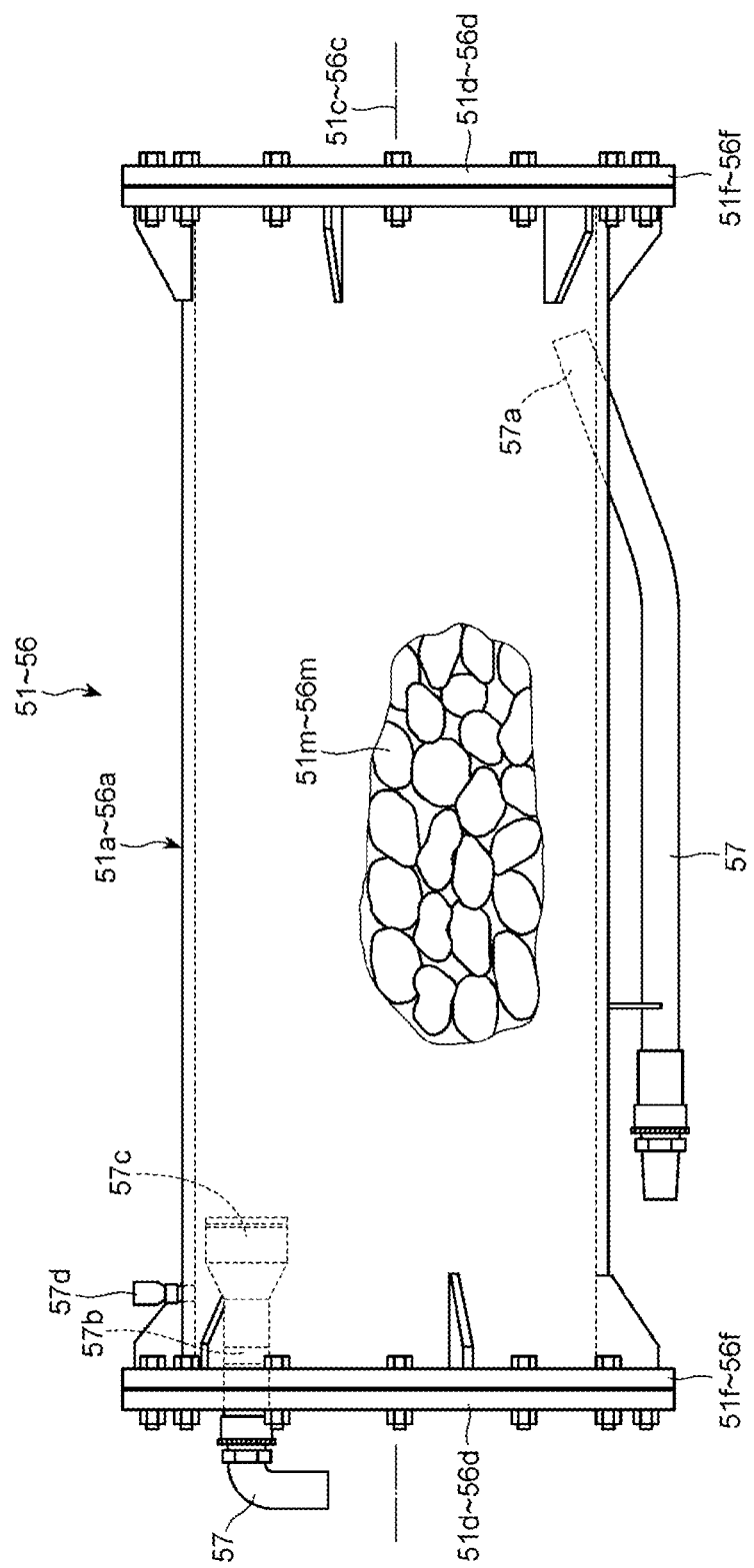
FIG. 11 is a side view of a water-passing container that constitutes the mineral-containing water (B) producing apparatus shown in FIG. 8.

In FIG. 8 through FIG. 10, the roundabout channels 51p-56p, the water stream-changing valves 51v-56v, the operation panel 58, and the signal cables 59, which have been mentioned above, are omitted therefrom.

As shown in FIG. 8 and FIG. 9, the mineral-containing water (B) producing apparatus 3 includes: the first water-passing container 51 through the sixth water-passing container 56 each of which has a cylindrical shape and have been mounted on the support frame 60; and the water supply passage 57 communicating in series the first water-passing container 51 through the sixth water-passing container 56, wherein the raw water tank 63 for storing water W supplied from waterworks is arranged at the top part of the support frame 60.

In the raw water tank 63, the inorganic porous body 64 having a function of adsorbing impurities in the water W therein is stored.

The casters 61 and the level adjusters 62 are provided with the bottom portion of the support frame 60.

The first water-passing container 51 through the sixth water-passing container 56, each of which is cylindrically shaped, are mounted on the support frame 60 having a rectangular parallelepiped lattice structure in a state where each of axial centers 51c-56c (See, FIG. 9) of the containers are kept horizontally.

The first water-passing container 51 through the sixth water-passing container 56 has been detachably attached onto the support frame 60.

As shown in FIG. 10, the first water-passing container 51 through the sixth water-passing container 56 has the same structure, respectively. Each airtight structure thereof is formed by attaching the disk shaped lid bodies 51d-56d to the flange parts 51f-56f provided with the both ends of the main body parts 51a-56a in cylindrical shapes.

At the lowest portion of the main body parts 51a-56a when the axial centers 51c-56c are in horizontal states, the water inlet 57a communicating with the water supply passage 57 is provided. At the highest portion (far from the water inlet 57a) of the lid bodies 51d-56d, the water outlet 57b communicating with the water supply passage 57 is provided. And, the mesh strainer 57c is attached to the water outlet 57b.

The automatic air valves 57d for releasing air in the first water-passing container 51 through the sixth water-passing container 56 are attached onto the outer peripheries (the directly above portions of the water outlet 57b) of the main body parts 51a-56a.

The water supplied from the water supply passage 57 in the upstream passes through the water inlet 57a, flows into the first water-passing container 51 through the sixth water-passing container 56, and contacts with the mineral-imparting material (B) 51m-56m with which have been filled up therein, respectively. Therefore, the respective mineral components elute into the water to form water containing mineral components corresponding to the mineral-imparting material (B) 51m-56m, and the formed water flows from the water outlet 57b into the water supply passage 57 in the downstream.

In the mineral-containing water (B) producing apparatus 3 shown in FIG. 8-FIG. 10, operating any of the switching buttons 51b-56b on the operation panel 58 shown in FIG. 7 to make the water W in the raw water tank 63 pass through at least one of the first water-passing container 51 through the sixth water-passing container 56 enables to produce the mineral-containing water (B) 45 into which the special respective mineral components contained in the mineral-imparting material (B) 51m-56m filled up within the first water-passing container 51 through the sixth water-passing container 56 have been selectively dissolved therein.

Since the first water-passing container 51 through the sixth water-passing container 56 are connected in series with the water supply passage 57 in the mineral-containing water (B) producing apparatus 3, continuously making water flow into the water supply passage 57 enables to mass-produce the mineral-containing water (B) 45 that the mineral components corresponding to the mineral-imparting material (B) 51m-56m in the first water-passing container 51 through the sixth water-passing container 56 have been dissolved therein.

The mineral-containing water (B) 45 produced by the mineral-containing water (B) producing apparatus 3 is transported from the sixth water-passing container 56 via the water supply passage 57x in the downstream thereof into the mixing tank 46, and is therein mixed to the mineral-containing water (A) 44 produced by the mineral-containing water (A) producing apparatus 2 shown in FIG. 1, thereby forming the mineral functional water 47.

The mixing ratio of the mineral-containing water (A) and the mineral-containing water (B) is suitably determined considering: the kind of material included in the mineral-containing water (A) and the mineral-containing water (B); and the density of eluted components.

The weight ratio (the mineral-containing water (A): the mineral-containing water (B)) of the mineral-containing water (A) and the mineral-containing water (B) is: within a range of 1:5-1:20; preferably within a range of 1:7-1:12; and more preferably within a range of 1:10.

Both in a first case where the mineral-containing waters (A) is too little (the mineral-containing waters (B) is too much) and in a second case where the mineral-containing waters (A) is too much (the mineral-containing waters (B) is to little), there is a possibility that effective components contained in the mineral functional water are so much diluted that objective action is insufficiently showed.

In the above, the preferable Embodiment of the method of producing the mineral functional water according to the present invention has been described. It is, however, sufficient that the mineral functional water according to the present invention including the above-mentioned configuration. Methods other than the above may be adopted instead thereof. In other words, it should be understood that the above description is not restrictive.

Especially, items that are not explicitly disclosed in the Embodiment, for example, operating conditions, running conditions, various parameters including a size of the elements, weight, volume, or the like do not deviate from a range where a person skilled in the art usually uses. Values capable of being easily assumed by the ordinary person skilled in the art are adopted.

EXAMPLES

Hereinafter, the present invention will now be more concretely explained adducing the following Examples. Needless to say, the present invention is NEVER limited to the Examples.

Example 1

[1. Manufacturing Mineral Functional Water]

The mineral functional water producing apparatus in the Embodiment and the producing method mentioned above have been used. And then, as the mineral functional water, the mineral functional water in Example 1 has been produced utilizing the following material and the following method.

1. Manufacturing Mineral-Containing Water (A)

Raw material for producing the mineral-imparting material (A) for the mineral-containing water (A) includes the vegetation raw material (A1) and the woody plant raw material (A2) shown below.

As the vegetation raw material (A1), "P-101 (lot number)" produced by Riken techno system Co., LTD. have been used. As the woody plant raw material (A2), "P-201 (lot number)" produced by Riken techno system Co., LTD. has been used.

"P-101" is the vegetation raw material (A1) produced by mixing the following dried pulverized product of Asteraceae plants and the following dried pulverized product of Rosaceae plants according to a weight ratio of 1:1, and "P-201" is the woody plant raw material (A2) described below. And, as sulfur raw material (A3), "S-100 (lot number)" produced by Riken techno system Co., LTD. have been used. Herein, "S-100" is powder composed of volcanic sulfur.

(A1) Vegetation Raw Material (Dried Vegetation Plants)

(A1-1) Dried Pulverized Product of Asteraceae Plants

This has been produced by: mixing 10 weight % of *Cirsium japonicum* (leaf parts, stem parts and flower parts thereof), 60 weight % of *Artemisia indica* (leaf parts and stem parts thereof) and 30 weight % of *Farfugium japonicum* (leaf parts and stem parts thereof); respectively to produce first mixture thereof; making the first mixture dry; and then pulverizing the dried first mixture.

(A1-2) Dried Pulverized Product of Rosaceae Plants

This has been produced by: mixing 20 weight % of *Rosa multiflora* (leaf parts and flower parts thereof), 10 weight % of *Geum japonicum* (leaf parts and stem parts thereof), and 70 weight % of *Rubus* L. (leaf parts, stem parts, and flower parts thereof); respectively to produce second mixture thereof; making the second mixture dry; and then pulverizing the dried second mixture.

(A2) Woody Plant Raw Material (Dried Woody Plants)

This has been produced by: mixing 20 weight % of *Maple* (leaf parts and stem parts thereof), 60 weight % of *Betula platyphylla* (leaf parts, stein parts, and bark parts thereof), and 20 weight % of *Cryptomeria japonica* (leaf parts, stem parts, and bark parts thereof); respectively to produce third mixture thereof; making the third mixture dry; and then pulverizing the dried third mixture.

(A3) Volcanic Sulfur Powder (Particle Diameter: About 10 Micrometers)

The mineral-imparting material (A) has been produced by:

mixing the vegetation raw material (A1) and the woody plant raw material (A2) according to a weight ratio of 1:5 to produce the mixture thereof; and based on 100 pts. wt. of the mixture, mixing 5 weight ratio of the volcanic sulfur (A3) to the mixture to produce the mineral-imparting material (A);

putting 10 to 15 weight % of the mineral-imparting material (A) based on the water into the raw mineral water solution production unit 10 (See, FIG. 2) of the mineral-containing water (A) producing apparatus 2 shown in FIG. 1;

conducting DC electric current having voltage of 8300 V and current of 100 mA has been conducted through the conductive wires of the raw mineral water solution production unit 10 to generate water flow around the conductive wires in the same direction as the DC electric current; and applying ultrasonic vibration (oscillating frequency of 50 kHz, amplitude of 1.5/1000 mm) to the water, thereby producing the raw mineral water solution (A).

Next, far-infrared rays (wavelength: 6-14 micrometers) have been irradiated to the mineral water solution (A) 41 supplied to the latter far-infrared ray-generating unit 43 to obtain the mineral-containing water (A).

2. Manufacturing Mineral-Imparting Material (B)

The raw material for producing the mineral-imparting material (B) for the mineral-containing water (B), which has been produced by: mixing the lime stone, the fossil coral, the shell, and the activated carbon to produce fourth mixture thereof; and then pulverizing the fourth mixture, has been used.

Material of the mineral-imparting material (B) and the mixture (mineral-imparting material (B1)-(B6)) used for the first passing container through the sixth water-passing container will now be explained as follows.

(1) Material (1-1) Lime stone: "CC-200 (lot number)" produced by Riken techno system Co., LTD.

The lime stone is a small stone produced by crushing a rock of lime in which volcanic ore deposits containing the following components are mixed into a size of about 3 cm: calcium carbonate: 50 weight % or more; iron oxide: 3 to 9 weight % of iron; and sum total of titanium oxide, titanium carbide, titanium nitride: 0.8 weight % or more, and magnesium carbonate: 7 to 10 weight %.

(1-2) "CC-300 (lot number)" produced by Riken techno system Co., LTD.

The fossil coral is granular material produced by mixing the following the two kinds of raw fossil coral according to a weight ratio of 1:9 to form mixture, and crushing the mixture into the size within 3-5 mm, the two kinds of raw fossil coral including: first fossil coral produced about 100 meters below the ground whose crystal construction has been denatured by pressure; and second fossil coral produced from land near Amamiohshima Island, Okinawa-Ken, Japan, and including: calcium carbonate; calcium phosphate; and other trace elements.

(1-3) Shell: "CC-400 (lot number)" produced by Riken techno system Co., LTD.

The shell is granular material produced by mixing ear shell, abalone, and acorn shell of the same weight to form mixture, and crushing the mixture into the size within 3-5 mm.

(1-4) Activated carbon (only used for the second water-passing container): "CC-500 (lot number)" produced by Riken techno system Co., LTD.

(2) Weight Ratios in the First Through the Sixth Water-Passing Containers

The first water-passing container:

The mineral-imparting material (B1) is mixture including: 70 weight % of lime stone; 15 weight % of fossil coral; and 15 weight % of shell.

The second water-passing container:

The mineral-imparting material (B2) is mixture including: 40 weight % of lime stone; 15 weight % of fossil coral; 40 weight % of shell; and 5 weight % of activated carbon, which corresponds to silicon dioxide and activated carbon.

The third water-passing container:

The mineral-imparting material (B3) is mixture including: 80 weight % of lime stone; 15 weight % of fossil coral; and 5 weight % of shell.

The fourth water-passing container:

The mineral-imparting material (B4) is mixture including: 90 weight % of lime stone; 5 weight % of fossil coral; and 5 weight % of shell.

The fifth water-passing container:

The mineral-imparting material (B5) is mixture including: 80 weight % of lime stone; 10 weight % of fossil coral; and 10 weight % of shell.

The sixth water-passing container:

The mineral-imparting material (B6) is mixture including: 60 weight % of lime stone; 30 weight % of fossil coral; and 10 weight % of shell.

In the mineral-containing water (B) producing apparatus 3 of the structure of FIG. 1, the mineral-containing water (B) has been obtained by make water pass through the first through the sixth water-passing containers which use the above-mentioned mineral-imparting material (B1)-(B6), respectively.

The respective mineral-imparting material (B1)-(B6) has the same weight of 50 kg (300 kg in total). And, the amount of the circulating water has been set up at 1000 kg, and the flow velocity thereof has been also set up at 500/40 mL/s.

The mineral-containing water (A) and the mineral-containing water (B) in Example 1 produced using the above-mentioned method have been mixed according to a weight ratio of 1:10 to obtain the mineral functional water in Example 1.

Utilizing a pH meter, which is a glass electrode type hydrogen-ion density indicator "TPX-90" manufactured by Tohkoh Chemical Laboratories, pH of the mineral functional water in Example 1 has been measured to be a pH value of 3.2

(Evaluation of Spectral Emissivity)

An evaluation sample of a dried body has been prepared by drying the powder containing mineral components of the mineral functional water in Example 1. And, the spectral emissivity of the sample has been measured with a far-infrared ray-radiating ratio-measuring apparatus (JIR-E500) produced by JEOL-Ltd.

The apparatus includes: a body of a Fourier transformed type infrared spectrophotometer (FTIR); a blackbody furnace; a sample-heating furnace; a temperature controller; and an attached optical system.

The evaluation sample with respect to spectral emissivity has been produced according to the following steps.

First, a predetermined amount of the mineral functional water in Example 1 has been evaporated on glass, and the dried body remaining thereon has been collected.

The collected dried body has been molded into a tablet form to be prepared for the measurement.

Figure 12:
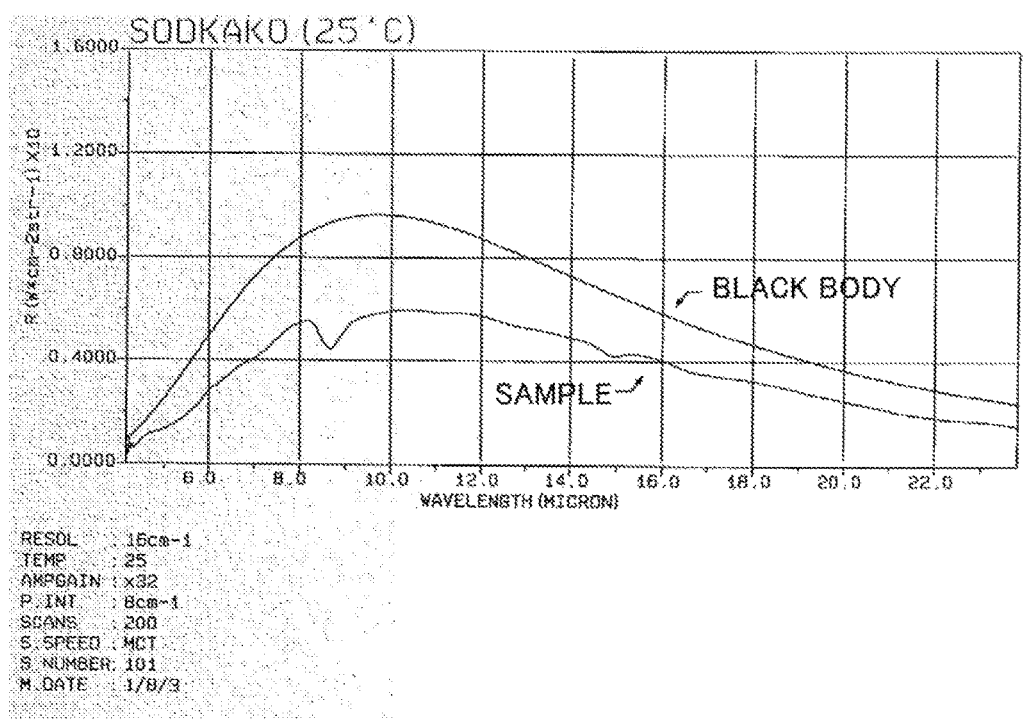
FIG. 12 shows spectral radiation spectra of the black body (theoretical values) and a sample (dried body) in Example 1 wherein 20 pts.wt. of mineral functional water in Example 1 is fixed based on 100 pts.wt. of ceramic carriers (measurement temperature: 25 Centigrade, range of wavelength: 4-24 micrometers, carrier: ceramic powder)

FIG. 12 shows the spectral radiation spectrum (measurement temperature: 25 Centigrade, wavelength: 4-24 micrometers) of the mineral functional water in Example 1 fixed onto the evaluation sample.

In addition, FIG. 12 also shows the spectral radiation spectrum (theoretical value) of the black body.

In FIG. 12, scales on the vertical axis indicate the strength of radiant energy using values (Watt) per square centimeters.

It means that the closer the measured curved line of the "evaluation sample" is to the theoretical curved line of the black body, the higher radiation power the evaluation sample possesses.

Figure 13:
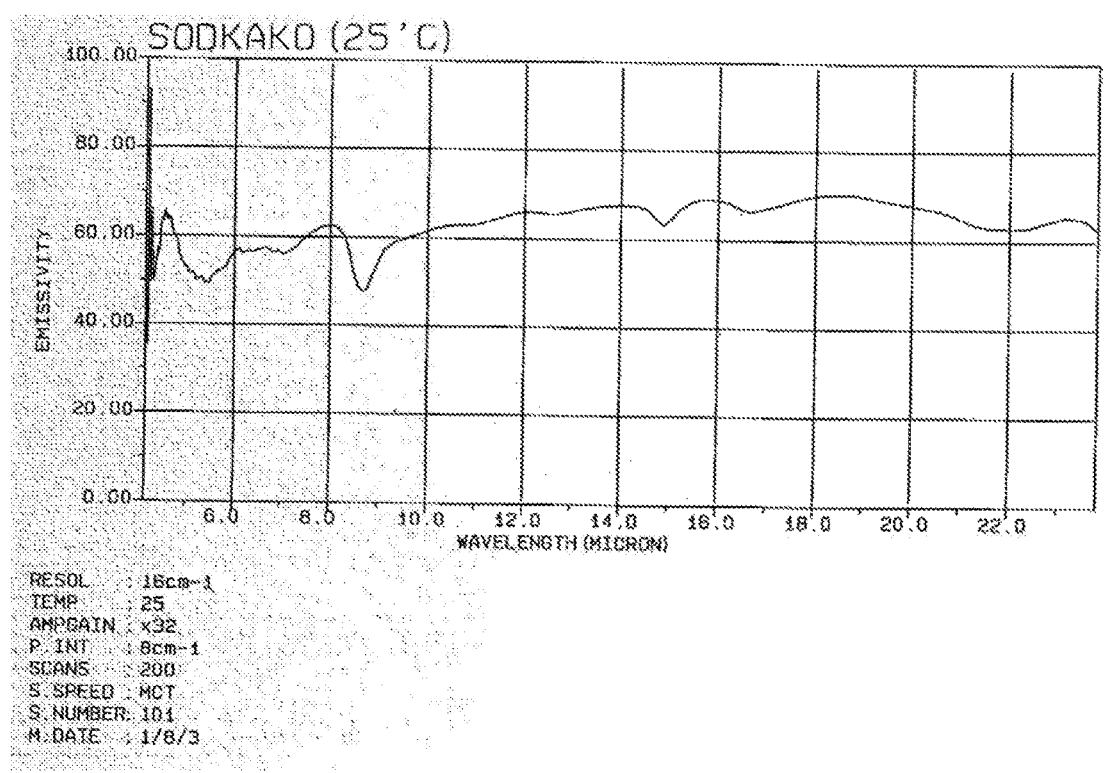
FIG. 13 is a graph showing emissivity (25 Centigrade) of the sample (dried body) in Example 1 based on the black body.

FIG. 13 shows the first spectral radiation spectrum of the measured sample and radiation ratios (wavelength range: 4-24 micrometers) calculated based on the spectral radiation spectrum (theoretical value) of the black body.

<2 Evaluation>

Evaluation 1: Evaluation of Antioxidation Activity

The evaluation 1 of the antioxidation activity of the mineral functional water in Example 1 has been made as follows.

That is, superoxide-scavenging activity (SOSA) on active oxygen has been evaluated according to the electron spin resonance (ESR) method.

First, as an evaluation sample, 20 [mL] of the mineral functional water in Example 1 has been precisely weighed to be filled an ESR tube up.

The ESR tube has been inserted into an ESR apparatus, and values of the SOSA have been measured utilizing a standard of manganese oxide.

As a comparative Example, the experiment has been performed similarly except for using distilled water.

Table 1 shows results thereof.

TABLE 1

| Sample | SOSA value (Unit/mL) |
| --- | --- |
| Example 1: | 3330 |
| Comparative Example: | 0.135 |

The mineral functional water in Example 1 has shown the SOSA value remarkably greater than that of the comparative Example.

Herein, it is considered that the SOSA value of vitamin C (pure powder) is about 3000 [Unit/mL]. Accordingly, it is apparent that the mineral functional water in Example 1 has superoxide-scavenging activity not less than that of vitamin C.

INDUSTRIAL APPLICABILITY

Because of having the excellent antioxidant effects and high safety to human, the mineral functional water according to the present invention can be utilized for various kinds of usage.

What is claimed is:

1. A method of producing mineral functional water, comprising:
   producing first mineral-containing water (A) according to a first process (1):
   producing second mineral-containing water (B) according to a second process (2): and
   mixing the first mineral-containing water (A) and the second mineral-containing water (B) according to a ratio within a range of 1: 5-1:20 (weight ratio), thereby producing the mineral functional water,
   wherein the first process (1) includes:
   immersing a conductive wire covered with insulator and mineral-imparting material ($\alpha$) into water, the mineral-imparting material ($\alpha$) containing: woody plant raw material; vegetation raw material; and sulfur raw material,
      wherein the vegetation raw material includes vegetation belonging to Asteraceae and vegetation belonging to Rosaceae, and
      wherein the woody plant raw material includes at least one kind selected from a group consisting of *Maple, Betula platyphylla, Pinus*, and *Cryptomeria japonica*;
   conducting DC electric current to the conductive wire to generate water flow around the conductive wire in the same direction as the DC electric current, applying ultrasonic vibration to the water, thereby forming raw mineral water solution (α); and irradiating rays (wavelength of 6-14 micrometers) to the raw mineral water solution (α) to form mineral-containing water (A), and wherein the second process (2) includes:

preparing a first water-passing container, a second water-passing container, a third water-passing container, a fourth water-passing container, a fifth water-passing container, and a sixth water-passing container, connected in series;

filling first mineral-imparting material (β1) into the first water-passing container, the first mineral-imparting material (β 1) including 70 weight % of lime stone, 15 weight % of fossil coral, and 15 weight % of shell of a shell fish;

filling second mineral-imparting material (β2) filled into the second water-passing container, the second mineral-imparting material (β2) including 40 weight % of lime stone, 15 weight % of fossil coral, 40 weight % of shell of a shell fish, and 5 weight % of activated carbon;

filling third mineral-imparting material (β3) into the third water-passing container, the third mineral-imparting material (β 3) including 80 weight % of lime stone, 15 weight % of fossil coral, and 5 weight % of shell of a shell fish;

filling fourth mineral-imparting material (β4) into the fourth water-passing container, the fourth mineral-imparting material (β 4) including 90 weight % of lime stone, 5 weight % of fossil coral, and 5 weight % of shell of a shell fish;

filling fifth mineral-imparting material (β5) into the fifth water-passing container, the fifth mineral-imparting material (β 5) including 80 weight % of lime stone, 10 weight % of fossil coral, and 10 weight % of shell of a shell fish;

filling sixth mineral-imparting material (β6) into the sixth water-passing container, the sixth mineral-imparting material (β 6) including 60 weight % of lime stone, 30 weight % of fossil coral, and 10 weight % of shell of a shell fish; and making water pass through the six water-passing containers to form the mineral-containing water (B).

2. The method of producing mineral functional water as defined in claim 1, wherein:

the immersing in the first process (1) is performed to produce water that contains 10 to 15 weight % of the mineral-imparting material (α); and the DC electric current conducted to the conductive wire has 0.05-0.1 A of a current value and 8000-8600 V of a voltage value.

3. The method of producing mineral functional water as defined in claim 1, wherein:

Asteraceae plant processed product and Rosaceae plant processed product are used as the mineral-imparting material (α);

the Asteraceae plant processed product is produced by:

mixing 10 weight % of *Cirsium japonicum* (leaf parts, stem parts and flower parts thereof), 60 weight % of *Artemisia indica* (leaf parts and stem parts thereof) and 30 weight % of *Farfugium japonicum* (leaf parts and stem parts thereof), to produce first mixture thereof; making the first mixture dry; and then pulverizing the dried first mixture;

the Rosaceae plant processed product is produced by:

mixing 20 weight % of *Rosa multiflora* (leaf parts and flower parts thereof), 10 weight % of *Geum japonicum* (leaf parts and stem parts thereof), and 70 weight % of *Rubus* L. (leaf parts, stem parts, and flower parts thereof), to produce second mixture thereof; making the second mixture dry; and then pulverizing the dried second mixture;

the Asteraceae plant processed product and the Rosaceae plant processed product are mixed according to 1:1 (weight ratio) to obtain vegetation raw material (α1);

the woody plant raw material (α2) is produced by:

mixing 20 weight % of *Maple* (fallen leaf parts and stem parts thereof), 60 weight % of *Betula platyphylla* (fallen leaf parts, stem parts, and bark parts thereof), and 20 weight % of *Cryptomeria japonica* (fallen leaf parts, stem parts, and bark parts thereof) to produce third mixture; making the third mixture dry; and then pulverizing the dried third mixture; and the sulfur raw material is composed of volcanic sulfur (α3); and mineral-imparting material (α') is obtained by:

mixing the vegetation raw material (α1) and the woody plant raw material (α2) according to 1:5 (weight ratio) to produce vegetation-woody plant raw material; and based on 100 pts.wt. of the vegetation-woody plant raw material, mixing 2-8 weight % of the volcanic sulfur (α3) thereto.

* * * * *